(12) United States Patent
Poitout et al.

(10) Patent No.: US 7,763,725 B2
(45) Date of Patent: Jul. 27, 2010

(54) PYRIMIDO-BENZIMIDAZOLE DERIVATIVES AND THE USE THEREOF IN THE FORM OF AGONISTS AND ANTAGONISTS OF MELANOCORTIN RECEPTORS

(75) Inventors: Lydie Poitout, Antony (FR); Carole Sackur, Paris (FR); Valerie Brault, Saint-Arnoult-Enyvelines (FR); Pierre Roubert, Paris (FR); Pascale Plas, Chatillon (FR)

(73) Assignee: Ipsen Pharma S.A.S., Boulogne-Billancourt (FR)

( * ) Notice: Subject to any disclaimer, the term of this patent is extended or adjusted under 35 U.S.C. 154(b) by 739 days.

(21) Appl. No.: 11/571,230

(22) PCT Filed: Jun. 22, 2005

(86) PCT No.: PCT/FR2005/001563

§ 371 (c)(1),
(2), (4) Date: May 18, 2007

(87) PCT Pub. No.: WO2006/010811

PCT Pub. Date: Feb. 2, 2006

(65) Prior Publication Data

US 2009/0209531 A1 Aug. 20, 2009

(30) Foreign Application Priority Data

Jun. 24, 2004 (FR) .................................. 04 06903

(51) Int. Cl.
*C07D 295/00* (2006.01)
*C07D 491/00* (2006.01)
*C07D 471/04* (2006.01)
*C07D 471/22* (2006.01)
*C07D 487/04* (2006.01)

(52) U.S. Cl. .................... 544/247; 544/115; 514/257

(58) Field of Classification Search .................. 544/247, 544/115; 514/257
See application file for complete search history.

(56) References Cited

U.S. PATENT DOCUMENTS

| 4,376,121 A | 3/1983 | Kienzle |
| 5,625,063 A | 4/1997 | Thurkauf et al. |
| 2002/0004512 A1 | 1/2002 | Bakshi et al. |

FOREIGN PATENT DOCUMENTS

| EP | 0311321 | 4/1989 |
| WO | WO/2006/010811 | 2/2006 |

*Primary Examiner*—Sreeni Padmanabhan
*Assistant Examiner*—Kendra D Carter
(74) *Attorney, Agent, or Firm*—Hunton & Williams LLP

(57) ABSTRACT

The invention relates to novel pyrimido-benzimidazole derivatives. Said products exhibit a good affinity for certain melanocortin receptor sub-types, in particular MC4 receptors. Said products represent a particular interest for treating pathological disorders and diseases associated with one or several melanocortin receptors. Pharmaceutical compositions containing said products and the use thereof for a drug preparation are also disclosed.

21 Claims, No Drawings

PYRIMIDO-BENZIMIDAZOLE DERIVATIVES AND THE USE THEREOF IN THE FORM OF AGONISTS AND ANTAGONISTS OF MELANOCORTIN RECEPTORS

FIELD OF INVENTION

A subject of the present application is novel pyrimido-benzimidazole derivatives. These products have a good affinity for certain melanocortin receptor subtypes, in particular MC4 receptors. They are particularly useful for treating pathological states and diseases in which one or more melanocortin receptors are involved. The invention also relates to pharmaceutical compositions containing said products and their use for the preparation of a medicament.

BACKGROUND OF INVENTION

The melanocortins represent a group of peptides which derive from the same precursor, proopiomelanocortin (POMC), and which are structurally similar: adrenocorticotropic hormone (ACTH), α-melanocyte-stimulating hormone (α-MSH), β-MSH and γ-MSH (Eipper B. A. and Mains R. E., *Endocr. Rev.* 1980, 1, 1-27). The melanocortins perform numerous physiological functions. They stimulate the synthesis of steroids by the adrenal cortex and the synthesis of eumelanin by the melanocytes. They regulate food intake, energy metabolism, sexual function, neuronal regeneration, blood pressure and heart rate, as well as pain perception, learning, attention and memory. The melanocortis also possess anti-inflammatory and anti-pyretic properties and control the secretion of several endocrine or exocrine glands such as the sebaceous, lachrymal, mammary glands, the prostate and the pancreas (Wikberg J. E. et al., *Pharmacol. Res.* 2000, 42, 393-420; Abdel-Malek Z. A., *Cell. Mol. Life. Sci.* 2001, 58, 434-441).

The effects of the melanocortins are mediated by a family of membrane receptors specific to seven transmembrane domains and S-protein-coupled. Five receptor subtypes, named MC1 to MC5, have been cloned and characterized to date. These receptors differ in their tissue distribution and affinity for the different melanocortins, the MC2 receptors recognizing only ACTH. The stimulation of the melanocortin receptors activates the adenylate cyclase with production of cyclic AMP. If the functional roles specific to each of the receptors are not totally elucidated, the treatment of pathological disorders or diseases can be associated with an affinity for certain subtypes of receptors. Thus the activation of the MC1 receptors has been associated with the treatment of inflammations, whereas blocking them has been associated with the treatment of cutaneous cancers. The treatment of nutritional disorders has been associated with the MC3 and MC4 receptors, the treatment of obesity by the agonists and the treatment of cachexia and anorexia by the antagonists. Other indications associated with the activation of the MC3 and MC4 receptors are sexual activity disorders, neuropathic pain, anxiety, depression and drug addiction. The activation of the MC5 receptors has been associated with the treatment of acne and dermatitis.

The applicants have found that the novel compounds of general formula (I) described hereafter possess a good affinity for the melanocortin receptors. They act preferentially on the MC4 receptors. Said compounds, melanocortin receptor agonists or antagonists, can be used in order to treat pathological states or metabolic diseases, of the nervous or dermatological system in which one or more melanocortin receptors are involved such as the following examples: inflammatory states, energy homeostasis disorders, food intake disorders, weight disorders (obesity, cachexia, anorexia), sexual activity disorders (erectile disorders), pain and more particularly neuropathic pain. Mental disorders can also be mentioned (anxiety, depression), drug addiction, skin diseases (acne, dermatitis, cutaneous cancers, melanomas). These compounds can also be used for stimulating nerve regeneration.

DETAILED DESCRIPTION OF THE INVENTION

A subject of the invention is therefore compounds of general formula (I)

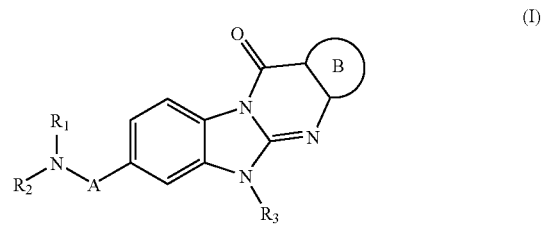

in racemic or enantiomeric form or any combinations of these forms and in which:

A represents —$CH_2$— or —C(O)—;

$R_1$ represents the hydrogen atom; a ($C_1$-$C_8$)alkyl radical optionally substituted by hydroxy or one or more identical or different halo radicals; ($C_2$-$C_6$)alkenyl; or a radical of formula —$(CH_2)_n$—$X_1$;

$R_2$ represents a ($C_1$-$C_8$)alkyl radical optionally substituted by hydroxy or one or more identical or different halo radicals; ($C_2$-$C_6$)alkenyl; or a radical of formula —$(CH_2)_n$—$X_1$;

each $X_1$ represents, independently, a ($C_1$-$C_6$)alkoxy, ($C_3$-$C_7$) cycloalkyl, adamantyl, heterocycloalkyl, aryl or heteroaryl radical, the ($C_3$-$C_7$)cycloalkyl, heterocycloalkyl, aryl and heteroaryl radicals being optionally substituted by one or more identical or different substituents chosen from: —$(CH_2)_{n'}$—$V_1$—$Y_1$, halo, nitro, cyano and aryl;

$V_1$ represents —O—, —S— or a covalent bond;

$Y_1$ represents a ($C_1$-$C_6$)alkyl radical optionally substituted by one or more identical or different halo radicals;

n represents an integer from 0 to 6 and n' an integer from 0 to 2 (it being understood that when n is equal to 0, then $X_1$ does not represent the alkoxy radical);

or $R_1$ and $R_2$ form, together with the nitrogen atom to which they are attached, a heterobicycloalkyl or a heterocycloalkyl optionally substituted by one or more identical or different substituents chosen from: hydroxy, ($C_1$-$C_6$)alkyl optionally substituted by hydroxy, ($C_1$-$C_6$)alkoxy-carbonyl, heterocycloalkyl and —C(O)—$NV_1'Y_1'$ with $V_1'$ and $Y_1'$ representing, independently, the hydrogen atom or a ($C_1$-$C_6$) alkyl; or a radical of formula:

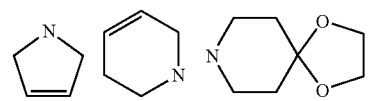

$R_3$ represents a radical of formula —$(CH_2)_s$—$R'_3$;

$R'_3$ represents the guanidino radical; a heterocycloalkyl containing at least one nitrogen atom and optionally substituted by ($C_1$-$C_6$)alkyl or aralkyl; a heteroaryl containing at least one nitrogen atom and optionally substituted by ($C_1$-$C_6$) alkyl; or a radical of formula —$NW_3W'_3$ $W_3$ represents the hydrogen atom or ($C_1$-$C_8$)alkyl;

$W'_3$ represents a radical of formula —$(CH_2)_{s'}$—$Z_3$;

$Z_3$ represents the hydrogen atom, ($C_1$-$C_8$)alkyl optionally substituted by one or more identical or different substituents chosen from: ($C_1$-$C_6$)alkoxy, ($C_1$-$C_6$)alkylthio and hydroxy; ($C_2$-$C_6$)alkenyl; ($C_3$-$C_7$)cycloalkyl optionally substituted by one or more identical or different ($C_1$-$C_6$)alkyl substituents; cyclohexene; heteroaryl and aryl;

the aryl and heteroaryl radicals being optionally substituted by one or more identical or different radicals chosen from: the radical of formula —$(CH_2)_{s''}$—$V_3$—$Y_3$, hydroxy, halo, nitro and cyano;

$V_3$ represents —O—, —S—, —NH—C(O)—, —$NV'_3$ or a covalent bond;

$Y_3$ represents a hydrogen atom or a ($C_1$-$C_6$)alkyl radical optionally substituted by one or more identical or different halo radicals;

$V_3'$ represents a hydrogen atom or a ($C_1$-$C_6$)alkyl;

s" represents an integer from 0 to 4;

or $Z_3$ represents a radical of formula

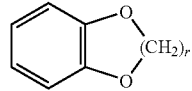

r = 1, 2 s and s' represent, independently, an integer from 0 to 6;

B represents a condensed, unsaturated, aromatic or non-aromatic mono- or bi-cyclic radical, optionally containing one or more identical or different heteroatoms chosen from O, S and N, and optionally substituted by one or more radicals, identical or different, chosen from: halo, nitro, cyano, oxy, —$X_B$—$Y_B$, and aryl optionally substituted by one or more substituents chosen from: halo and ($C_1$-$C_6$)alkyl optionally substituted by one or more identical or different halo radicals;

$X_B$ represents a covalent bond, —O—, —S—, —C(O)—, —$NR_N$—C(O)—, —C(O—$NR_N$—, —C(O)—O—, —$SO_2$— or —$SO_2NH$—;

$Y_B$ represents the hydrogen atom or a ($C_1$-$C_6$)allyl radical optionally substituted by one or more identical or different halo radicals;

$R_N$ represents the hydrogen atom or a ($C_1$-$C_6$)alkyl radical;

or a pharmaceutically acceptable salt thereof.

In the definitions given above, the expression halo represents the fluoro, chloro, bromo or iodo radical, preferably chloro, fluoro or bromo. The expression alkyl (unless otherwise stated), preferably represents an alkyl radical having 1 to 6 carbon atoms, linear or branched, such as the methyl, ethyl, propyl, isopropyl, butyl, isobutyl, sec-butyl and tert-butyl, pentyl or amyl, isopentyl, neopentyl, 2,2-dimethyl-propyl, hexyl, isohexyl or 1,2,2-trimethyl-propyl radicals. The term ($C_1$-$C_8$)alkyl designates an alkyl radical having 1 to 8 carbon atoms, linear or branched, such as the radicals containing 1 to 6 carbon atoms as defined above but also heptyl, octyl, 1,1,2, 2-tetramethyl-propyl, 1,1,3,3-tetramethyl-butyl. The expression alkyl substituted by hydroxy should be understood to mean any linear or branched alkyl chain, containing a hydroxy radical positioned along the chain; thus for a chain containing 3 carbon atoms and a hydroxy radical, the examples HO—$(CH_2)_3$—, $CH_3$—CH(OH)—$CH_2$— and $CH_3$—$CH_2$—CH(OH)— may be given.

By alkenyl, unless otherwise stated, is meant a linear or branched alkyl radical containing 2 to 6 carbon atoms and having at least one unsaturation (double bond), such as for example vinyl, allyl, propenyl, butenyl or pentenyl.

The term alkoxy designates the radicals in which the alkyl radical is as defined above such as for example the methoxy, ethoxy, propyloxy or isopropyloxy radicals but also linear, secondary or tertiary butoxy, pentyloxy. The term alkoxycarbonyl preferably designates the radicals in which the alkoxy radical is as defined above such as for example methoxycarbonyl, ethoxycarbonyl. The term alkylthio designates the radicals in which the alkyl radical is as defined above such as for example methylthio, ethylthio. The term guanidino represents the —NHC(=NH)$NH_2$ radical.

The term ($C_3$-$C_7$)cycloalkyl designates a saturated carbonaceous monocyclic system comprising 3 to 7 carbon atoms, and preferably the cyclopropyl, cyclobutyl, cyclopentyl, cyclohexyl or cycloheptyl rings. The expression heterocycloalkyl designates a condensed monocyclic or bicyclic saturated system containing 2 to 9 carbon atoms and at least one heteroatom. This radical can contain several identical or different heteroatoms. Preferably, the heteroatoms are chosen from oxygen, sulphur or nitrogen. As an example of heterocycloalkyl, the following may be mentioned: rings with 5 or 6 members containing at least one nitrogen atom such as pyrrolidine, imidazolidine, pyrazolidine, isothiazolidine, thiazolidine, isoxazolidine, oxazolidine, piperidine, piperazine, morpholine, rings with more than 6 members and containing at least one nitrogen atom such as azepane (azacycloheptane), azacyclooctane, diazepane, decahydroisoquinoline (or decahydroquinoline), but also the rings containing no nitrogen atom such as tetrahydrofuran (tetrahydrofuryl radical) or tetrahydrothiophene (tetrahydrothienyl radical).

The term heterobicycloalkyl designates an non-condensed saturated bicyclic hydrocarbon system containing 5 to 8 carbon atoms and at least one heteroatom chosen from nitrogen, oxygen and sulphur. As examples of heterobicycloalkyl, aza-bicycloheptane and aza-bicyclooctane such as 7-aza-bicyclo [2,2,1]heptane, 2-aza-bicyclo[2,2,2]octane or 6-aza-bicyclo [3,2,1]octane may be mentioned.

The expression aryl represents an aromatic radical, constituted by a ring or condensed rings, such as for example the phenyl, naphthyl, fluorenyl or anthryl radical.

The expression heteroaryl designates an aromatic radical, constituted by a ring or condensed rings, with at least one ring containing one or more identical or different heteroatoms chosen from sulphur, nitrogen or oxygen. As examples of a heteroaryl radical, the radicals containing at least one nitrogen atom such as pyrrolyl, imidazolyl, pyrazolyl, isothiazolyl, thiazolyl, isoxazolyl, oxazolyl, oxadiazolyl, triazolyl, thiadiazolyl, pyridyl, pyrazinyl, pyrimidyl, pyridazinyl, quinolyl, isoquinolyl, quinoxalinyl, indolyl, benzoxadiazolyl, carbazolyl, phenoxazinyl, thieno-pyridinyl (thieno[2,3-b]pyridine, thieno[3,2-b]pyridine, thieno[2,3-c]pyridine, thieno[3,2-c]pyridine, thieno[3,4-b]pyridine, thieno[3,4-c] pyridine), thieno-pyrazinyl (thieno[2,3-b]pyrazine, thieno[3, 4-b]pyrazine) but also the radicals not containing a nitrogen atom such as thienyl, benzothienyl, furyl, benzofuryl, dibenzofuryl, dihydrobenzofuryl, dibenzothienyl, thioxanthenyl, or pyranyl can be mentioned.

The term aralkyl (arylalkyl) preferably designates the radicals in which the aryl and alkyl radicals are as defined above such as for example benzyl or phenethyl.

The expression aromatic, unsaturated, condensed, mono- or bi-cyclic radical, can be illustrated either by the aryl radical as defined above when said aromatic radical does not contain a heteroatom, or by the heteroaryl radical as defined above when said aromatic radical contains at least one heteroatom.

The expression non-aromatic, unsaturated, condensed, mono- or bi-cyclic radical not containing any heteroatom, can be illustrated by cyclopentenyl or cyclohexenyl.

The expression non-aromatic unsaturated, condensed, mono- or bi-cyclic radical containing at least one heteroatom, can be illustrated by the heteroaryl radicals as defined above and in which at least one double bond is hydrogenated. There may thus be mentioned as examples the radicals associated with the following rings: dihydroindolyl, dihydrothiophene (2,5-dihydrothiophene, 2,3-dihydrothiophene), tetrahydropyridine (2,3,4,5-tetrahydropyridine, 1,2,3,6-tetrahydropyridine, 1,2,3,4-tetrahydropyridine), tetrahydro-thieno-pyridine (4,5,6,7-tetrahydro-thieno[3,2-b]pyridine, 4,5,6,7-tetrahydro-thieno[2,3-c]pyridine, 4,5,6,7-tetrahydrothieno[3,2-c]pyridine), tetrahydropyrimidine (2,3,4,5-tetrahydropyrimidine, 1,2,3,4-tetrahydropyrimidine, 1,4,5,6-tetrahydropyrimidine), tetrahydrobenzothiophene (4,5,6,7-tetrahydro-1-benzothiophene), dihydrocyclopentathiophene (5,6-dihydro-4H-cyclopenta[b]thiophene, benzodioxole, dihydro-benzodioxin.

In the present application also, the —$(CH_2)_i$— radical (i integer being able to represent n, n', s, s' and s'', as defined above), represents a hydrocarbon chain, linear or branched, with i carbon atoms. Thus the —$(CH_2)_3$— radical can represent —$CH_2$—$CH_2$—$CH_2$— but also —$CH(CH_3)$—$CH_2$—, —$CH_2$—$CH(CH_3)$— or —$C(CH_3)_2$—.

According to the present application also, when a radical has the formula —B-D-E with D representing for example —C(O)—NH—, this means that the carbon atom of —C(O)—NH— is linked to B and the nitrogen atom to E.

Preferably, the invention relates to compounds of formula I as defined above and characterized in that A represents —C(O)—; or a pharmaceutically acceptable salt thereof.

Preferably also, the invention relates to compounds of formula I as defined above, characterized in that $R_1$ and $R_2$ represent, independently, a $(C_1-C_8)$alkyl; or a pharmaceutically acceptable salt thereof.

Very preferably, the invention relates to compounds of formula I as defined above, characterized in that $R_1$ and $R_2$ represent, independently, a $(C_1-C_6)$alkyl radical, and more particularly $R_1$ and $R_2$ represent, independently, a butyl, pentyl or isopentyl radical; or a pharmaceutically acceptable salt thereof.

Preferably also, the invention relates to compounds of formula I as defined above, characterized in that $R'_3$ represents a heterocycloalkyl containing at least one nitrogen atom and optionally substituted by $(C_1-C_6)$alkyl or benzyl; or a radical of formula —$NW_3W'_3$ in which $W_3$ represents the hydrogen atom or a $(C_1-C_8)$alkyl radical, and $W'_3$ the $Z_3$ radical and $Z_3$ represents the hydrogen atom or a $(C_1-C_8)$alkyl radical; or a pharmaceutically acceptable salt thereof.

Preferably also, the invention relates to compounds of formula I as defined above, characterized in that B represents a radical chosen from: phenyl, thienyl, pyrrolyl, pyrazolyl, pyridyl, pyrimidyl, pyrazinyl, benzothienyl, thieno-pyridinyl, thieno-pyrazinyl, indolyl, benzofuryl, cyclopentenyl, cyclohexenyl, 1,2,3,6-tetrahydropyridinyl, 1,2,3,4-tetrahydropyrimidinyl, 4,5,6,7-tetrahydrothieno[2,3-c]pyridinyl, tetrahydrobenzothienyl and dihydtocyclopentathienyl.

Preferably also, the invention relates to compounds of formula I as defined above, characterized in that B is optionally substituted by one or more radicals, identical or different, chosen from: halo, nitro, cyano, oxy, —$X_B$—$Y_B$, and phenyl optionally substituted by one or more substituents chosen from: halo and $(C_1-C_6)$alkyl optionally substituted by one or more identical or different halo radicals;

$X_B$ represents a covalent bond, —O—, —S—, —C(O)—, —$NR_N$—C(O)— or —C(O)—O—;

$Y_B$ represents the hydrogen atom or a $(C_1-C_6)$alkyl radical optionally substituted by one or more identical or different halo radicals;

$R_N$ represents the hydrogen atom; or a pharmaceutically acceptable salt thereof.

Preferably also, the invention relates to compounds of formula I as defined above, characterized in that B represents a radical chosen from: phenyl, furyl, thienyl, pyrrolyl, pyrazolyl, pyridyl, thiazolyl, pyrazinyl, benzothienyl, thieno-pyridinyl, thieno-pyrazinyl, indolyl, benzofuryl, cyclohexenyl, 1,2,3,6-tetrahydropyridinyl, tetrahydrobenzothienyl and dihydrocyclopentathienyl.

Preferably also, the invention relates to compounds of formula I as defined above, characterized in that B is optionally substituted by one or more radicals, identical or different, chosen from: halo, nitro, cyano, —$X_B$—$Y_B$, and phenyl optionally substituted by one or more substituents chosen from: halo and $(C_1-C_6)$alkyl;

$X_B$ represents a covalent bond, —O—, —S—, —C(O)— or —C(O)—O—;

$Y_B$ represents the hydrogen atom or a $(C_1-C_6)$alkyl radical; or a pharmaceutically acceptable salt thereof.

Preferably also, the invention relates to compounds of formula I as defined above, characterized in that B represents a radical chosen from: phenyl, furyl, thienyl, pyrrolyl pyrazolyl, pyridyl, pyrazinyl, benzothienyl, thieno-pyridinyl, indolyl, benzofuryl, cyclohexenyl, 1,2,3,6-tetrahydropyridinyl, tetrahydrobenzothienyl and dihydrocyclopentathienyl.

Preferably also, the invention relates to compounds of formula I as defined above, characterized in that B is optionally substituted by one or more radicals, identical or different, chosen from: halo, nitro and —$X_B$—$Y_B$;

$X_B$ represents a covalent bond, —O—, —C(O)— or —C(O)—O—;

$Y_B$ represents a $(C_1-C_6)$alkyl radical;

and very preferably B is optionally substituted by one or more radicals, identical or different, chosen from: halo, nitro or —$X_B$—$Y_B$; $X_B$ represents a covalent bond or —O— and $Y_B$ represents a $(C_1-C_6)$alkyl radical; or a pharmaceutically acceptable salt thereof.

Very preferably, the invention relates to compounds of formula I as defined above, characterized in that $R'_3$ represents a heterocycloalkyl containing at least one nitrogen atom and optionally substituted by $(C_1-C_6)$alkyl, and in particular the piperidinyl or pyrrolidinyl radical; or a pharmaceutically acceptable salt thereof.

Preferably also, the invention relates to compounds of formula I as defined above, characterized in that $R'_3$ represents a heterocycloalkyl with 5 to 6 members and IQ containing a single nitrogen atom and optionally an oxygen atom; or a radical of formula —$NW_3W'_3$ in which $W_3$ represents the hydrogen atom or a $(C_1-C_6)$alkyl radical, $W'_3$ represents the $Z_3$ radical and $Z_3$ represents the hydrogen atom or a $(C_1-C_6)$ alkyl radical; or a pharmaceutically acceptable salt thereof.

Very preferably also, the invention relates to compounds of formula I as defined above, characterized in that $R'_3$ represents the piperidinyl or pyrrolidinyl radical, and s represents an integer from 2 to 4; or a pharmaceutically acceptable salt thereof.

Very preferably also, the invention relates to compounds of formula I as defined above, characterized in that B represents a radical chosen from: phenyl, thienyl, pyrrolyl, pyrazolyl, pyridyl, pyrazinyl, benzothienyl, thieno-pyridinyl, thieno-pyrazinyl, indolyl, benzofuryl, cyclohexenyl, 4,5,6,7-tetrahydro-thieno[2,3-c]pyridinyl and dihydrocyclopentathienyl.

According to the definitions of the variable groups A, B, $R_1$, $R_2$ and $R_3$, the compounds according to the invention can be prepared in liquid phase according to the different procedures A to C described below.

A. Preparation According to Reaction Diagram:

The compounds of formula (I) according to the invention in which A represents —C(O)—, can be prepared according to the following diagram A:

a primary amine in the presence of an inorganic base such as cesium or potassium carbonate in an inert organic solvent such as dimethylformamide or acetonitrile at a temperature of 20-100° C. for 2 to 48 hours produces derivative (4). The nitro function of compound (4) is reduced by treatment with stannous chloride dihydrate in an inert solvent such as ethyl acetate or dimethylformamide at a temperature of 60-80° C. for 3 to 15 hours, or by catalytic hydrogenation in the presence of 10% palladium on charcoal in an inert solvent such as methanol, ethanol, ethyl acetate or a mixture of these solvents, at a temperature of 18-25° C., for 2 to 8 hours in order to produce dianiline (5). The derivative (5) is then treated with an ortho-ester isothiocyanate in the presence of a coupling agent supported on a resin or not such as diisopropylcarbo-

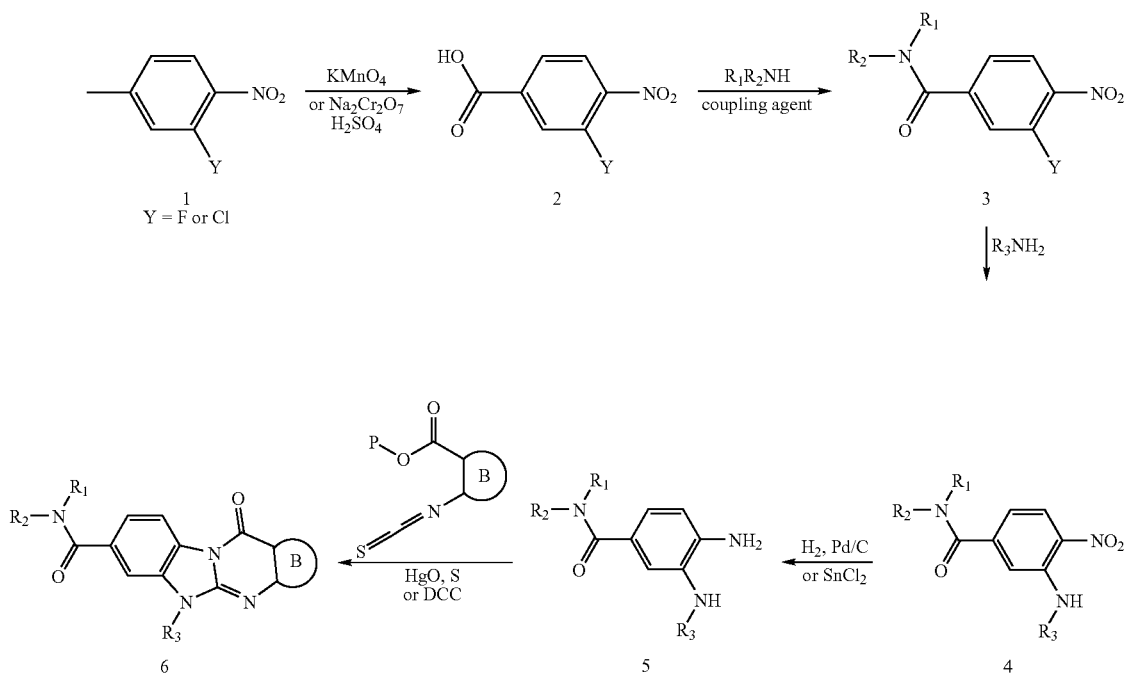

P = protection group (Me, Et, tBu ... )

As described in diagram A, the methylated derivative (1) can be oxidized in carboxylic acid (2) with an aqueous solution of potassium permanganate at a temperature of 100° C. for 3 to 6 hours (according to the procedure of Schmelkes et au, *J. Am. Chem. Soc,* 1944, 1631), or by an aqueous solution of sodium dichromate in the presence of sulphuric acid at a temperature of 20-90° C. for 1 to 3 hours (according to the procedure of Howes et al, *European J. Med. Chem.,* 1999, 34, 225-234). The carboxylic acid (2) can be coupled with a primary or secondary amine in the presence of a coupling agent such as diisopropylcarbodiimide (DIC), dicyclohexylcarbodiimide (DCC), 1-3-dimethylaminopropyl)-3-ethylcarbodiimide hydrochloride (EDC) or carbonyldiimidazole (CDI) with or without 1-hydroxybenzotriazole (HOBt) in an inert organic solvent such as methylene chloride, tetrahydrofuran or dimethylformamide at ambient temperature for 3 to 24 hours in order to produce the corresponding amide (3). Treatment of the fluorinated or chlorinated derivative (3) with diimide or dicyclohexylcarbodiimide or N-methylcyclohexylcarbodiimide N-methyl polystyrene resin, in the presence or not of an organic base such as triethylamine, diisopropylethylamine, sodium methylate, ethylate or tert-butylate, in an inert solvent such as tetrahydrofuran, methylene chloride, or chloroform at a temperature of 20-70° C. for 2 to 72 hours, or under microwaves (Personal Chemistry® equipment), in a sealed tube, at 100° C. for 10 to 30 minutes in order to produce the derivative (6). Alternatively, the derivative (5) can be treated with an ortho-ester isothiocyanate in the presence of yellow mercury (II) oxide and a catalytic quantity of sulphur, in the presence or not of an organic base such as triethylamine, diisopropylethylamine, sodium methylate, ethylate or tert-butylate, in a polar solvent such as methanol or ethanol for 2 to 24 hours at a temperature of 20-80° C., or under microwaves (Personal Chemistry® equipment), in a sealed tube, at 100° C. for 10 to 30 minutes in order to produce (6).

EXAMPLE A1

N,N-bis(3-methylbutyl)-11-oxo-5-(3-piperidin-1-ylpropyl)-5,11-dihydrothieno[3',2':4,5]pyrimido[1,2-a]benzimidazole-7-carboxamide hydrochloride

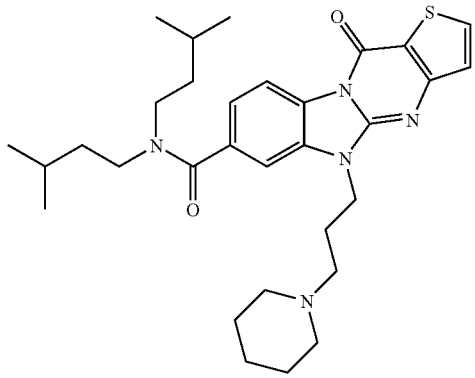

Stage 1: 3-fluoro-4-nitrobenzoic acid

A mixture of 3-fluoro-4-nitrotoluene (10 g, 1 eq) and potassium permanganate (25.5 g, 2.5 eq) in water (1 L) is heated under reflux for 6 hours then cooled down to ambient temperature. The mixture is filtered on celite and the aqueous phase is washed twice with diethyl ether (2×300 ml). The aqueous phase is acidified, at 0° C., with a solution of concentrated hydrochloric acid then concentrated under reduced pressure at 40° C. to a volume of approximately 300 ml. The precipitate formed is filtered then washed with petroleum ether and dried in order to produce the expected compound in the form of a white solid (6.9 g; 58% yield).

NMR ($^1$H, 400 MHz, DMSO-$d_6$): δ 7.93 (m, 2H), 8.25 (m, 1H), 13.95 (m, 1H).

Stage 2: 3-fluoro-N,N-bis(3-methylbutyl)-4-nitrobenzamide 1-hydroxybenzotriazole (HOBt) (8 g, 1.1 eq) in solution in THF (60 ml) and 1-(3-dimethylaminopropyl)-3-ethylcarbodiimide hydrochloride (EDC) (11.4 g, 1.1 eq) in solution in chloroform (60 ml) are added successively to 3-fluoro-4-nitrobenzoic acid (10 g, 1 eq) in solution in anhydrous THF (60 ml). The mixture is stirred for 2 hours at a temperature of approximately 20° C. then diisoamylamine (12.2 ml, 1.1 eq) is added. After stirring for 4 hours at a temperature of approximately 20° C., the reaction mixture is concentrated under reduced pressure at 40° C. The residue is taken up in dichloromethane (300 ml) and water (100 ml). After decantation and extractions, the combined organic phases are washed with salt water, dried over $Na_2SO_4$ then concentrated under reduced pressure at 40° C. Purification by flash chromatography on silica gel (eluent: heptane 100% to heptane/ ethyl acetate 70:30) produces the expected compound (12.36 g; 71% yield).

MS/LC: MM calculated 324.4; m/z=325.2 (MH+)

NMR ($^1$H, 400 MHz, DMSO-$d_6$): δ 0.69 (d, 6H), 0.93 (d, 6H), 1.35-1.60 (m, 6H), 3.09 (m, 2H), 3.41 (m, 2H), 7.38 (AB, 1H), 7.63 (AB, 1H), 8.21 (t, 1H).

Stage 3: N,N-bis(3-methylbutyl)-4-nitro-3-[(3-piperidin-1-ylpropyl)amino]benzamide A mixture of 3-fluoro-N,N-bis(3-methylbutyl)-4-nitrobenzamide (4 g, 1 eq), 3-aminopropylpiperidine (1.9 g, 1.1 eq) and potassium carbonate (3.4 g, 2 eq) in acetonitrile (150 ml) is heated under reflux for 3 hours then concentrated under reduced pressure at 40° C. The residue is taken up in dichloromethane (200 ml) and water (80 ml). After decantation and extractions, the combined organic phases are washed with salt water, dried over $Na_2SO_4$ then concentrated under reduced pressure at 40° C. Purification of the residue by flash chromatography on silica gel (eluent: ethyl acetate 100% to ethyl acetate/methanol 80:20) produces the expected compound in the form of a yellow oil (5.5 g; 100% yield).

MS/LC: MM calculated 446.6; m/z=447.3 (MH+)

NMR ($^1$H, 400 MHz, DMSO-$d_6$): δ 0.68 (d, 6H), 0.92 (d, 6H), 1.31-1.69 (m, 12H), 1.74 (m, 2H), 2.32 (m, 6H), 3.10 (t, 2H), 3.38 (m, 4H), 6.53 (AB, NH), 6.91 (s, 1H), 8.09 (d, 1H), 8.44 (t, 1H).

Stage 4: 4-amino-N,N-bis(3-methylbutyl)-3-[(3-piperidin-1-ylpropyl)amino]benzamide N,N-bis(3-methylbutyl)-4-nitro-3-[(3-piperidin-1-ylpropyl)amino]benzamide (1 g) in solution in a mixture of ethyl acetate/ethanol 2:1 (100 ml) and 10% palladium on charcoal (100 mg) are introduced into an autoclave. After stirring for 3 hours under a hydrogen atmosphere (3 bars) at a temperature of approximately 20° C., the catalyst is eliminated by filtration on celite and the filtrate is concentrated under reduced pressure at 40° C. in order to produce the expected compound in the form of an oil (910 mg, 97% yield).

MS/LC: MM calculated 416.6; m/z=417.3 (MH+)

NMR ($^1$H, 400 MHz, DMSO-$d_6$): δ 0.81 (d, 12H), 1.39-1.69 (m, 12H), 1.73 (m, 2H), 2.32 (m, 6H), 3.03 (m, 2H), 3.38 (m, 4H), 4.62 (s, 1H), 4.76 (s, 2H), 6.36 (s, 1H), 6.42 (AB, 1H), 6.50 (AB, 1H).

Stage 5: N,N-bis(3-methylbutyl)-11-oxo-5-(3-piperidin-1-ylpropyl)-5,11-dihydrothieno[3',2':4,5]pyrimido[1,2-a]benzimidazole-7-carboxamide hydrochloride Methyl 3-isothiocyanatothiophene-2-carboxylate (890 mg), yellow mercury II oxide (1.6 g) and sulphur (30 mg) are added successively to a solution of 4-amino-N,N-bis(3-methylbutyl)-3-[(3-piperidin-1-ylpropyl)amino]benzamide (1.55 g) in methanol (20 ml). The mixture is heated under reflux for 16 h. After cooling, the mixture is filtered on celite and the filtrate is concentrated under reduced pressure at 40° C. Purification of the residue by flash chromatography on silica gel (eluent: dichloromethane 100% to dichloromethane/methanol 95:5) produces the expected compound in the form of the free base. The corresponding hydrochloride salt is formed by adding a 1N HCl solution in ethyl ether to the free base solution in ethyl acetate. The precipitate obtained is filtered and dried in order to produce the expected hydrochloride compound (920 mg).

MS/LC: MM calculated=550.3; m/z=549.8 (MH+)

NMR ($^1$H, 400 MHz, DMSO-$d_6$) δ 0.68 (s, 6H), 0.95 (s, 6H), 1.25-1.80 (m, 12H), 2.27 (m, 2H), 2.80 (m, 2H), 3.18 (m,

4H), 3.35 (d, 2H), 3.45 (m, 2H), 4.43 (t, 2H), 7.32 (AB, 1H), 7.35 (AB, 1H), 7.77 (s, 1H), 8.25 (AB, 1H), 8.52 (AB, 1H), 9.72 (s, 1H).

EXAMPLE A2

N,N-bis(3-methylbutyl)-12-oxo-5-(3-piperidin-1-ylpropyl)-5,12-dihydro[1]benzothieno[3',2':4,5]pyrimido[1,2-a]benzimidazole-3-carboxamide hydrochloride

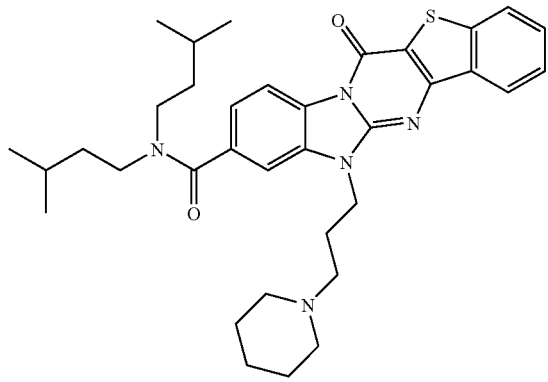

A solution of 4-amino-N,N-bis(3-methylbutyl)-3-[(3-piperidin-1-ylpropylamino]benzamide (62 mg) in tetrahydrofuran (1 ml) and a solution of methyl 3-isothiocyanatothiophene-2-carboxylate (45 mg) in tetrahydrofuran (1 ml) are added successively to a suspension of N-methylcyclohexylcarbodiimide-N-methyl polystyrene resin (265 mg, 1.7 mmol/g charge, 3 eq) in tetrahydrofuran (1 ml), placed in a "Personal Chemistry®" reaction tube. The tube is sealed with a cap, placed in the "Personal Chemistry®" microwave and heated under magnetic stirring at 100° C. for 15 minutes. The mixture is then filtered and the filtrate is concentrated under reduced pressure at 40° C. A solution of the residue in methanol (3 ml) and triethylamine (30 mg) is placed in a "Personal Chemistry®" reaction tube and heated in the microwave under magnetic stirring at 100° C. for 10 minutes. The mixture is then concentrated under reduced pressure at 40° C. Purification of the residue by flash chromatography on silica gel (eluent: dichloromethane 100% to dichloromethane/methanol 90:10) produces the expected compound in the form of the free base. The corresponding hydrochloride salt is formed by adding a 1N HCl solution in ethyl ether to the free base solution in ethyl acetate. The precipitate obtained is filtered and dried in order to produce the expected hydrochloride compound (55 mg).

MS/LC: MM calculated=600.4; m/z=599.8 (MH+)

NMR ($^1$H, 400 MHz, DMSO-$d_6$): δ 50.68 (s, 6H), 0.96 (s, 6H), 1.21-1.81 (m, 12H), 2.20 (m, 4H), 3.20 (m, 2H), 3.30 (m, 2H), 3.45 (m, 2H), 4.54 (t, 2H), 7.37 (AB, 1H), 7.61 (m, 1H), 7.69 (m, 1H), 7.81 (s, 1H), 8.14 (AB, 1H), 8.32 (AB, 1H), 8.58 (AB, 1H), 9.1 (s, 1H).

Preparation of Non-Commercial Isothiocyanates

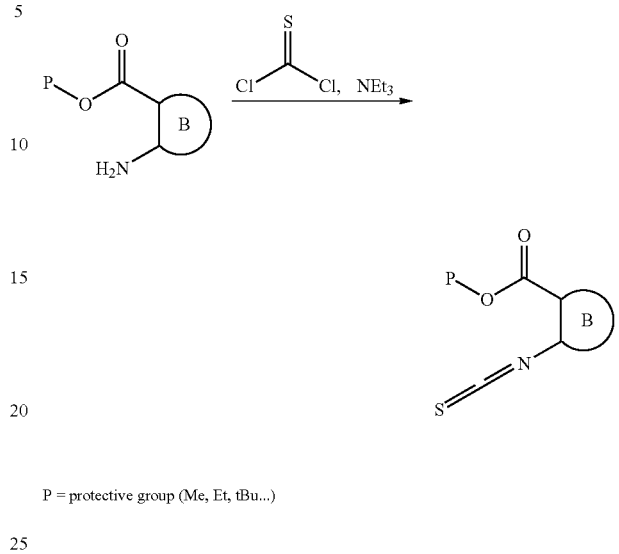

P = protective group (Me, Et, tBu...)

A primary amine can be converted to isothiocyanate, by treatment with thiophosgene in the presence of a tertiary base such as triethylamine, diisopropylethylamine, in an aprotic solvent such as dichloromethane or tetrahydrofuran, at a temperature of 0-20° C. for 0.1 to 2 hours.

Preparation of methyl 3-isothiocyanatothiophene-2-carboxylate

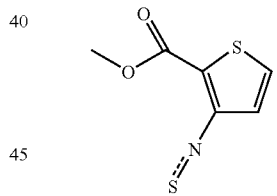

Thiophosgene (1.1 mL, 1.1 eq) is added dropwise to a solution cooled down to 0° C. of 3-amino-2-thiophenecarboxylate (2 g, 1 eq) and triethylamine (3.9 g, 3 eq in tetrahydrofuran (100 ml). The mixture is stirred for 15 min at 0° C. then water (70 ml) and diethyl ether (150 ml) are added. After decantation and extractions, the organic phases are combined, washed with salt water, dried over $Na_2SO_4$ then concentrated under reduced pressure at 40° C. Purification of the residue by flash chromatography on silica gel (eluent: heptane 100% to heptane/ethyl acetate 7:3) produces the expected compound in the form of a beige powder (2.15 g, 85% yield).

NMR ($^1$H, 400 MHz, DMSO-$d_6$): δ 3.84 (s, 3H), 7.26 (d, 1H), 7.98 (d, 1H).

The following isothiocyanates were prepared according to a procedure similar to that described for methyl 3-isothiocyanatothiophene-2-carboxylate:

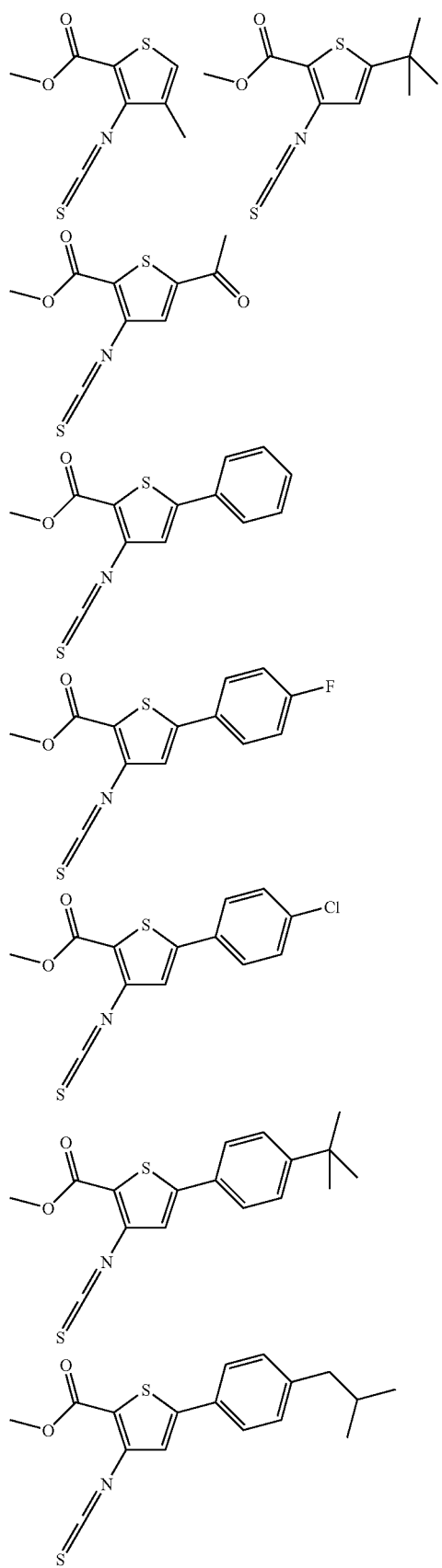
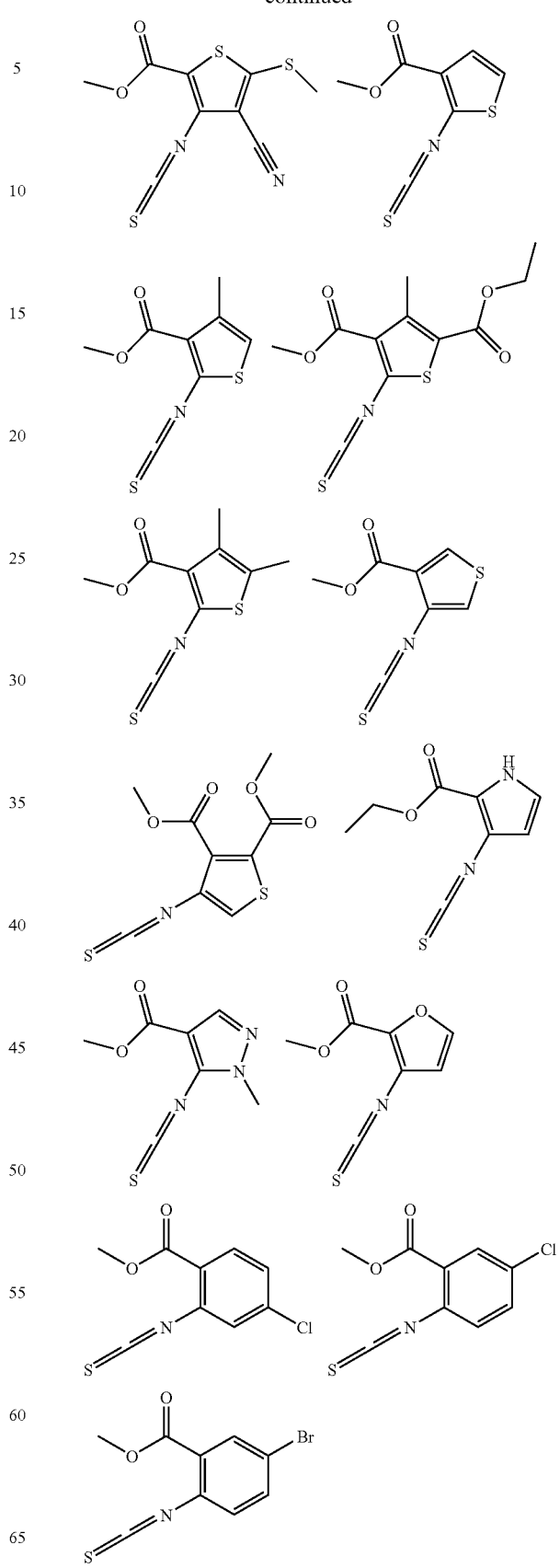

-continued
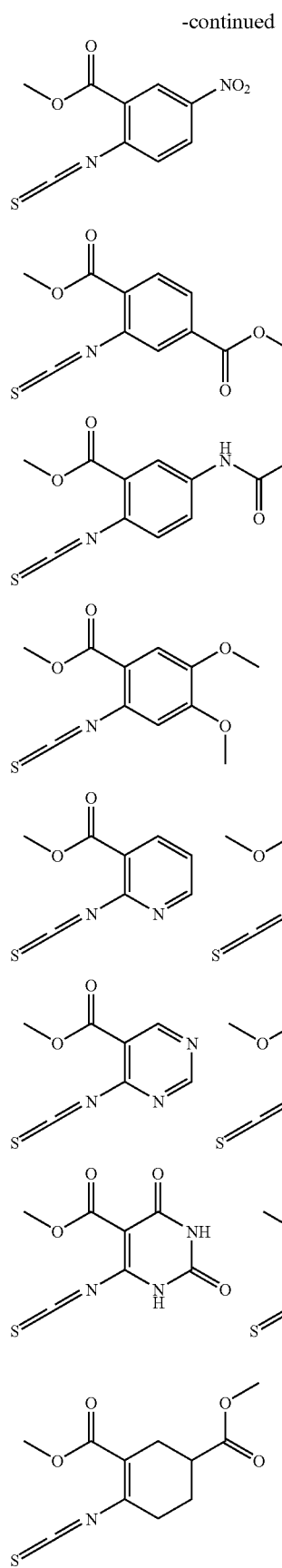
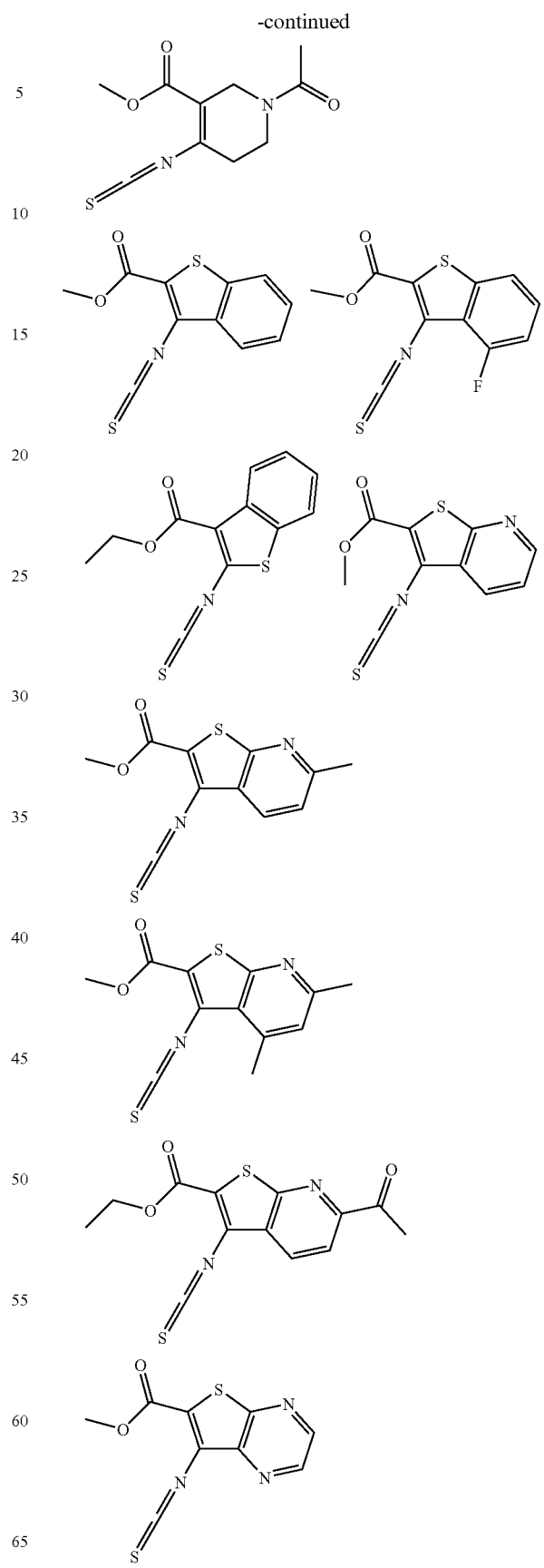

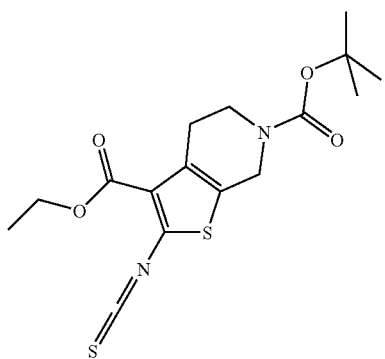

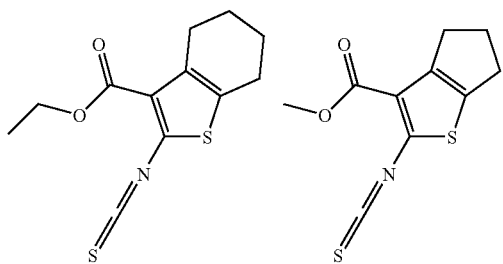

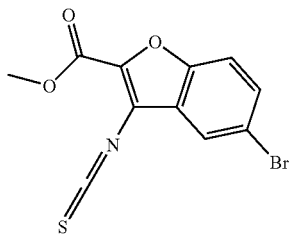

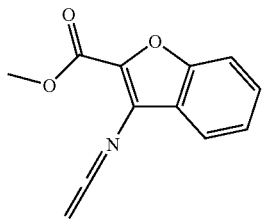

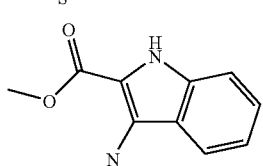

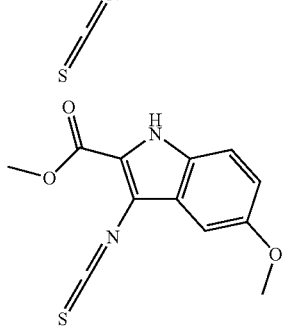

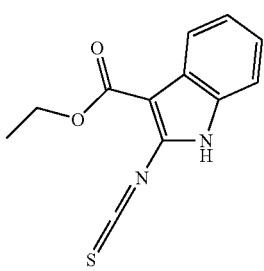

According to reaction diagram A and in a manner similar to the procedure described for the synthesis of N,N-bis(3-methylbutyl)-11-oxo-5-(3-piperidin-1-ylpropyl)-5,11-dihydrothieno[3',2':4,5]pyrimido[1,2-a]benzimidazole-7-catoxamide hydrochloride or N,N-bis(3-methylbutyl)-12-oxo-5-(3-piperidin-1-ylpropyl)-5,12-dihydro[1]benzothieno[3',2':4,5]pyrimido[1,2-a]benzimidazole-3-carboxamide hydrochloride, the following compounds have been prepared:

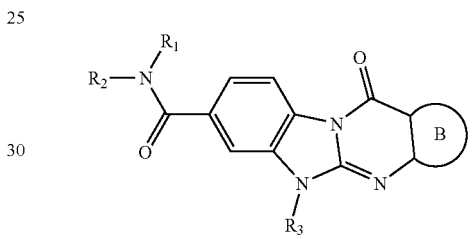

in which $R_1R_2N$ represents one of the following radicals:

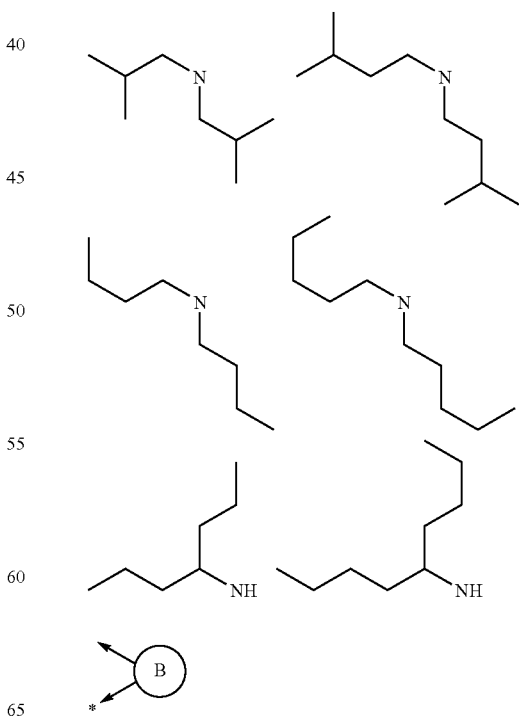

represents one of the following radicals:
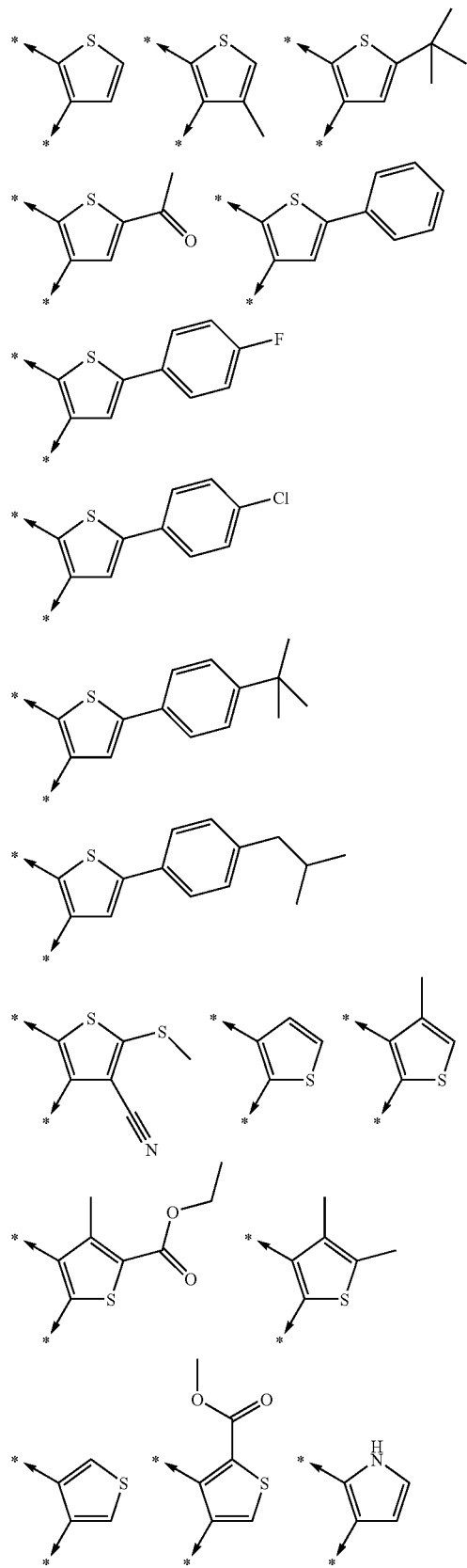
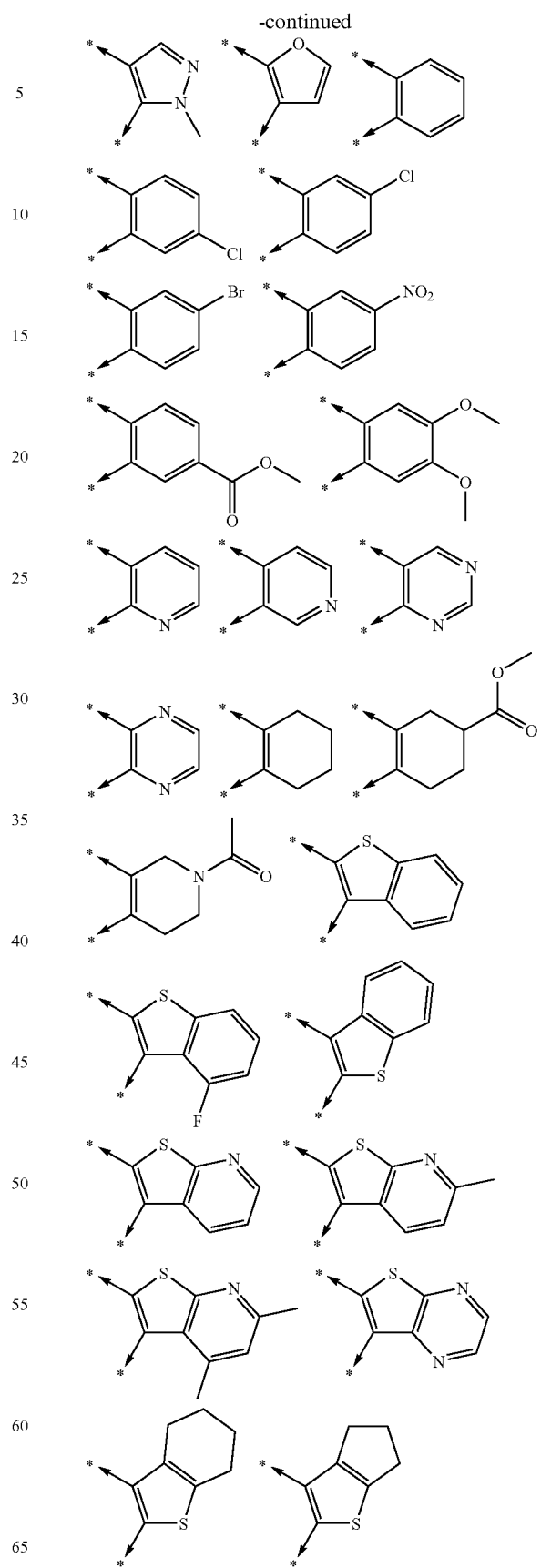

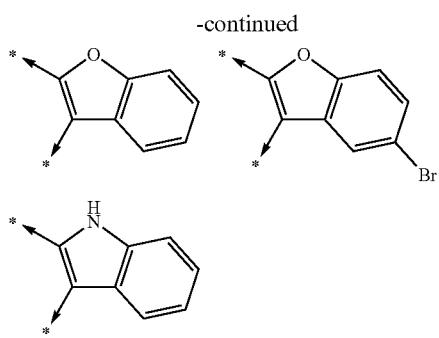
and R₃ represents one of the following radicals:
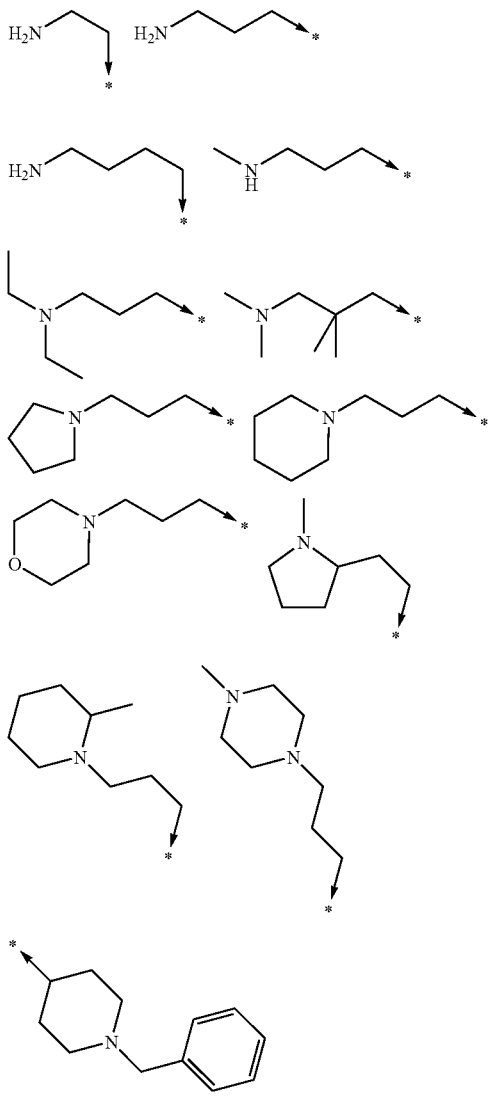
B. Preparation According to Reaction Diagram B:
The compounds of formula (I) according to the invention in which A represents —C(O)—, can be also prepared according to the following diagram B:
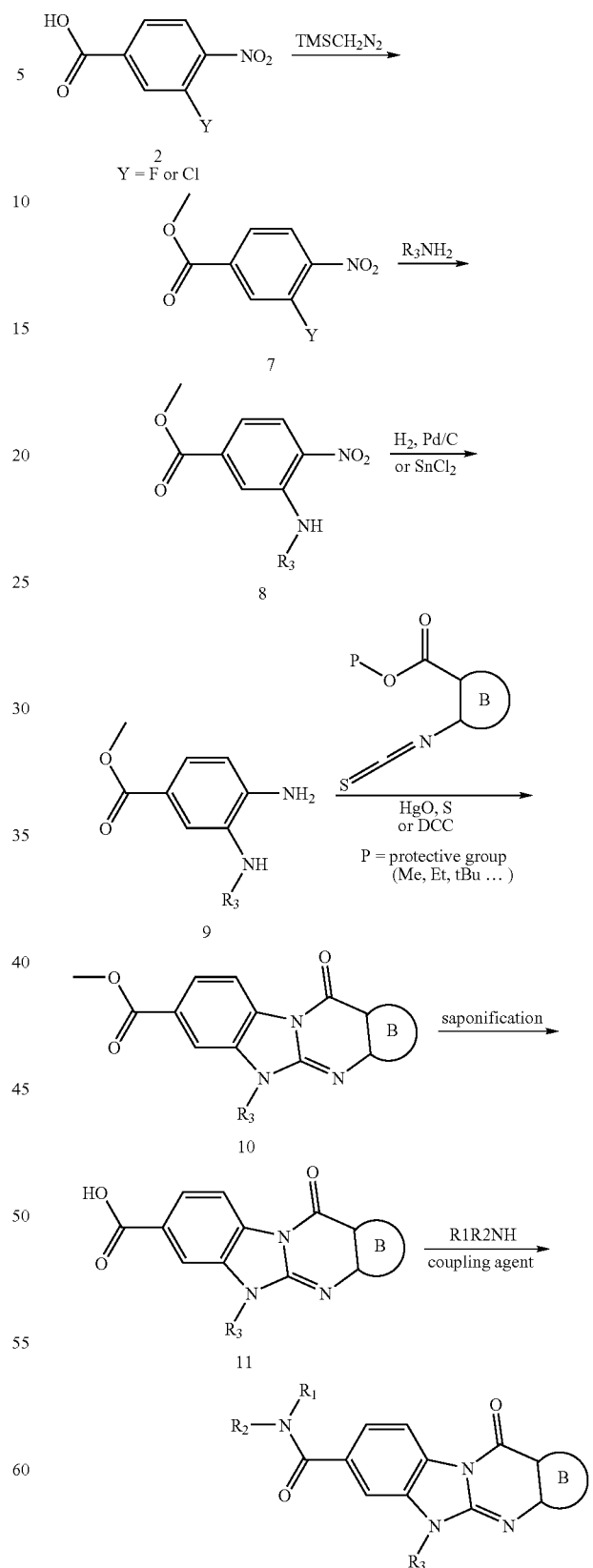

As described in diagram B, carboxylic acid (2) can be converted to methyl ester (7) either by treatment with a trimethylsilyl-diazomethane solution at a temperature of 0-20° C., or by formation of a carboxylate salt using an inorganic base such as lithium hydroxide dihydrate or cesium carbonate, at ambient temperature for 30 mm to 2 hours, in an inert organic solvent such as tetrahydrofuran, followed by the addition of dimethylsulphate at ambient temperature and stirring under reflux for 5 to 15 hours. The fluorinated or chlorinated derivative (7) can be treated with a primary amine in the presence of an inorganic base such as cesium or potassium carbonate in an inert organic solvent such as dimethylformamide or acetonitrile at a temperature of 20-100° C. for 2 to 48 hours in order to produce the derivative (8). The nitro function of compound (8) can be reduced by treatment with stannous chloride dihydrate in an inert solvent such as ethyl acetate or dimethylformamide, at a temperature of 60-80° C. for 3 to 15 hours, or by catalytic hydrogenation in the presence of 10% palladium on charcoal in an inert solvent such as methanol, ethanol, ethyl acetate or a mixture of these solvents, at a temperature of 18-25° C., for 2 to 8 hours, in order to produce dianiline (9). The derivative (9) is then treated with an ortho-ester isothiocyanate in the presence of a coupling agent supported on a resin or not such as diisopropylcarbodiimide or dicyclohexylcarbodiimide or N-methylcyclohexylcarbodiimide N-methyl polystyrene resin, in the presence or not of an organic base such as triethylamine or diisopropylethylamine, in an inert solvent such as tetrahydrofuran, methylene chloride, or chloroform at a temperature of 20-70° C. for 2 to 12 hours, or under microwaves (Personal Chemistry® equipment), in a sealed tube, at 100° C. for 10 to 30 minutes in order to produce the derivative (10). Alternatively, the derivative (9) can be treated with an ortho-ester isothiocyanate in the presence of yellow mercury (II) oxide and a catalytic quantity of sulphur, in the presence or not of an organic base such as triethylamine, diisopropylethylamine, sodium methylate, ethylate or tert-butylate, in a polar solvent such as methanol or ethanol for 2 to 24 hours at a temperature of 20-80° C., or under microwaves (Personal Chemistry® equipment), in a sealed tube, at 100° C. for 10 to 30 minutes in order to produce (10). The methyl ester (10) can then be saponified in the presence of an inorganic base such as lithium hydroxide dihydrate in a mixture of polar solvents such as water and tetrahydrofuran at a temperature of 20 to 70° C. for 3 to 17 hours. The resulting carboxylic acid (11) can be coupled with a primary or secondary amine in the presence of a coupling agent such as diisopropylcarbodiimide (DIC), dicyclohexylcarbodiimide (DCC), 1-(3-dimethylaminopropyl)-3-ethylcarbodiimide (EDC) hydrochloride or carbonyldiimidazole (CDI), with or without 1-hydroxybenzotriazole (HOBt) in an inert organic solvent such as methylene chloride, tetrahydrofuran or dimethylformamide at ambient temperature for 3 to 24 hours in order to produce the corresponding amide (6).

C. Preparation According to Reaction Diagram C:

The compounds of formula (I) according to the invention in which A represents —$CH_2$—, can be prepared according to the following diagrams C and C':

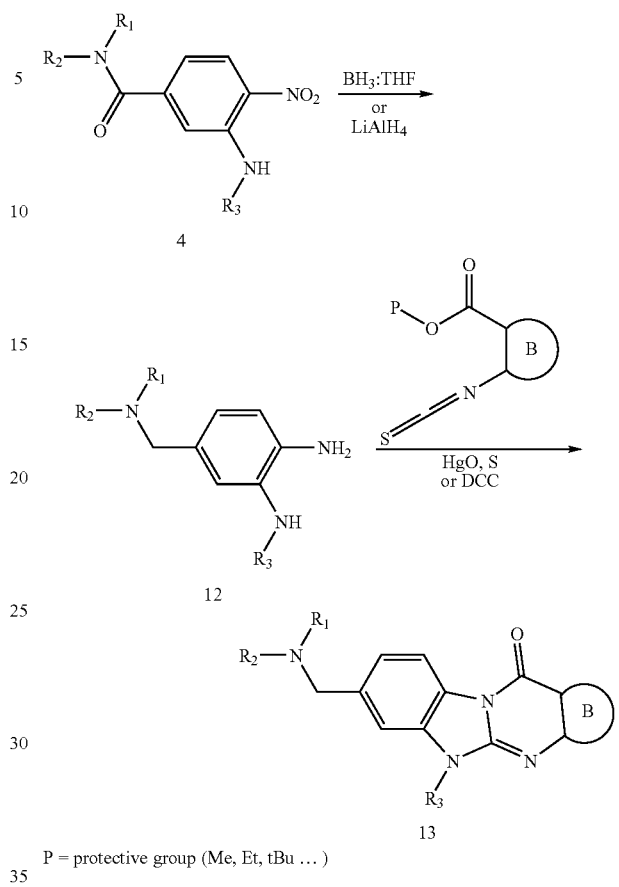

P = protective group (Me, Et, tBu ... )

As described in diagram C, the derivative (4) prepared according to reaction diagram A, can be reduced to the compound (12) using borane or lithium aluminium hydride in an aprotic solvent such as tetrahydrofuran or diethyl ether at a temperature of 0 to 70° C., for 18 to 24 hours. Dianiline (12) can then be treated with an ortho-ester isothiocyanate in the presence of a coupling agent supported on a resin or not such as diisopropylcarbodiimide or dicyclohexylcarbodiimide or N-methylcyclohexylcarbodiimide N-methyl polystyrene resin, in the presence or not of an organic base such as triethylamine or diisopropylethylamine, in an inert solvent such as tetrahydrofuran, methylene chloride, or chloroform at a temperature of 20-70° C. for 2 to 72 hours, or under microwaves (Personal Chemistry® equipment), in a sealed tube, at 100° C. for 10 to 30 minutes in order to produce the derivative (13). Alternatively, the derivative (12) can be treated with an ortho-ester isothiocyanate in the presence of yellow mercury (11) oxide and a catalytic quantity of sulphur, in the presence or not of an organic base such as triethylamine, diisopropylethylamine, sodium methylate, ethylate or tert-butylate, in a polar solvent such as methanol or ethanol for 2 to 24 hours at a temperature of 20-80° C., or under microwaves (Personal Chemistry® equipment), in a sealed tube, at 100° C. for 10 to 30 minutes in order to produce (13).

Preparation According to Reaction Diagram C':

The compounds (13) can also be prepared according to the following diagram C':

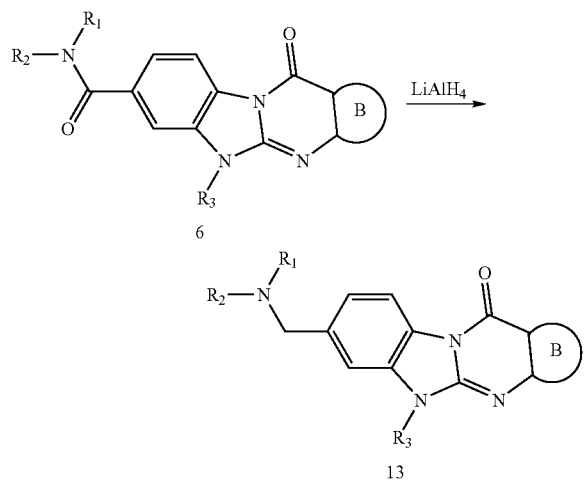

As described in diagram C', the amide (6) prepared according to reaction diagrams A or B, can be reduced to the corresponding amine (13) using borane or lithium aluminium hydride in an aprotic solvent such as tetrahydrofuran or diethyl ether at a temperature of 0 to 70° C., for 1 to 6 hours.

EXAMPLE C1

8-{[bis(3-methylbutyl)amino]methyl}-10-(3-piperidin-1-ylpropyl)thieno[2',3':4,5]pyrimido[1,2-a]benzimidazol-4(10H)-one dihydrochloride

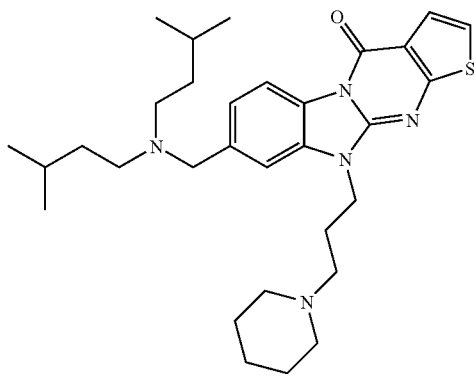

Stage 1: 4-{[bis(3-methylbutyl)amino]methyl}-N²-(3-piperidin-1-ylpropyl)benzene-1,2-diamine A lithium aluminium hydride solution (36 ml; 1N in THF) is added dropwise to a solution cooled down to 0° C. of N,N-bis(3-methylbutyl)-4-nitro-3-[(3-piperidin 1-ylpropyl)amino]benzamide (1.6 g). The mixture is returned to a temperature of 20° C. then heated under reflux for 6 hours and hydrolyzed with water cooled down to 0° C. followed by a 1N soda solution. After the addition of dichloromethane, the mixture is filtered on celite. After decantation of the filtrate and extractions, the combined organic phases are washed with 1N soda then with salt water, dried over $Na_2SO_4$ and concentrated under reduced pressure at 40° C. in order to produce the expected compound in the form of an oil (1.23 g, 85% yield).

MS/LC: MM calculated=402.7; m/z=403.3 (MH+)

NMR ($^1$H, 400 MHz, DMSO-d$_6$): δ 0.81 (d, 12H), 1.28 (m, 4H), 1.38 (m, 2H), 1.48 (m, 6H), 1.71 (m, 2H), 2.31 (m, 10H), 3.01 (m, 2H), 3.29 (m, 2H), 4.28 (m, 2H), 4.6 (m, 1H), 6.30 (AB, 1H), 6.38 (s, 1H), 6.43 (AB, 1H).

Stage 2: 8-{([bis(3-methylbutyl)amino]methyl}-10-(3-piperidin-1-ylpropyl)thieno[2',3':4,5]pyrimido[1,2-a]benzimidazol-4(10i f)-one dihydrochloride Methyl 2-isothiocyanatothiophene-3-carboxylate (45 mg), yellow mercury II oxide (65 mg) and sulphur (3 mg) are added successively to a solution of 4-amino-N,N-bis(3-methylbutyl)-3-[(3-piperidin-1-ylpropyl)amino]benzamide (60 mg) in methanol (3 ml). The mixture is heated under reflux for 16 h. After cooling, the mixture is filtered over celite and the filtrate is concentrated under reduced pressure at 40° C. Purification of the residue by flash chromatography on silica gel (eluent:dichloromethane 100% to dichloromethane/methanol 90:10) produces the expected compound in the form of the free base. The corresponding hydrochloride salt is formed by adding a 1N HCl solution in ethyl ether to the free base solution in ethyl acetate. The precipitate obtained is filtered and dried in order to produce the expected hydrochloride compound (30 mg).

MS/LC: MM calculated=536.4; m/z=535.8 (MH+)

NMR ($^1$H, 400 MHz, DMSO-d$_6$): δ 0.86 (d, 12H), 1.30 (m, 2H), 1.54 (m, 2H), 1.68 (m, 8H), 2.39 (m, 2H), 2.78 (m, 2H), 3.01 (m, 4H), 3.19 (m, 2H), 3.38 (m, 2H), 4.37 (t, 2H), 4.48 (m, 2H), 7.37 (AB, 1H), 7.54 (AB, 1H), 8.26 (AB, 1H), 8.30 (s, 1H), 8.51 (AB, 1H), 9.97 (s, 1H), 10.96 (s, 1H).

The following compounds have been prepared according to reaction diagrams C or C':

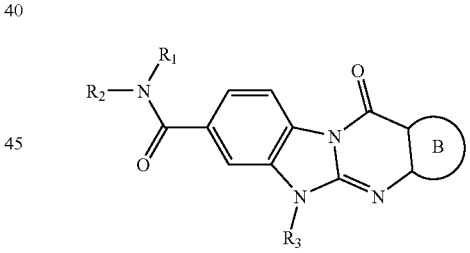

in which $R_1R_2N$ represents one of the following radicals:

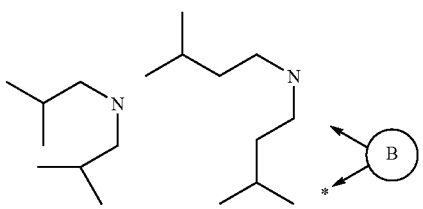

represents one of the following radicals:

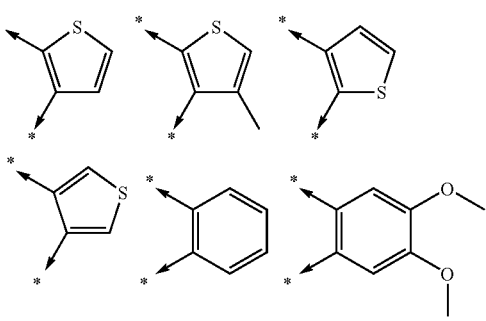

and R_3 represents one of the following radicals:

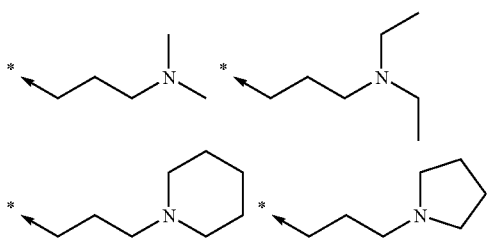

A subject of the invention is also a method for the preparation of a compound of formula (I) as defined above, characterized in that the compound of general formula:

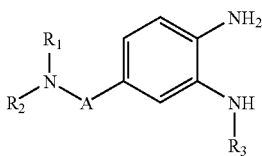

in which A, $R_1$, $R_2$, $R_3$ have the meaning given above, is treated with an ortho-ester isothiocyanate of general formula

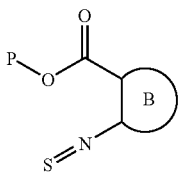

in which P is a protective group such as methyl, ethyl, tert-butyl and B has the meaning given above in the presence of a coupling agent or yellow mercury (II) oxide in the presence of sulphur, in a protic or aprotic solvent, in the presence or not of a base. The reaction can be carried out at a temperature of 50 to 80° C. for a period of 3 to 48 hours. The reaction can also be carried out under microwaves, in a sealed tube, at a temperature of 80-120° C., for 5 to 30 minutes.

The coupling agent can be supported such as N-methylcyclohexylcarbodiimide N-methyl polystyrene resin or not supported such as diisopropylcarbodiimide, diethylcarbodiimide or dicyclohexylcarbodiimide. A protic solvent such as methanol or ethanol or an aprotic solvent such as tetrahydrofuran or acetonitrile can be used. The base can be triethylamine, diisopropylethylamine, sodium methylate, ethylate or tert-butylate.

The compounds I of the present invention possess useful pharmacological properties. Thus it has been discovered that the compounds I of the present invention possess a good affinity for certain subtypes of melanocortin receptors, in particular MC4 receptors.

The compounds of the present invention can thus be used in different therapeutic applications. They can advantageously be used for the treatment of pathological conditions or diseases in which one or more melanocortin receptors are involved such as inflammatory conditions, weight disorders (obesity, cachexia, anorexia), sexual activity disorders (erectile disorders), pain, but also mental disorders (anxiety, depression), drug addiction, skin diseases (acne, dermatitises, melanomas). An illustration of the pharmacological properties of the compounds of the invention will be found hereafter, in the experimental part.

A subject of the present application is also pharmaceutical compositions containing, as active ingredient, at least one product of formula I as defined above, as well as the pharmaceutically acceptable salts of said product of formula I, in combination with a pharmaceutically acceptable support.

By pharmaceutically acceptable salt, is meant in particular addition salts of inorganic acids such as hydrochloride, hydrobromide, hydroiodide, sulphate, phosphate, diphosphate and nitrate or organic acids such as acetate, maleate, fumarate, tartrate, succinate, citrate, lactate, methanesulphonate, p-toluenesulphonate, pamoate and stearate. Salts formed from bases such as sodium or potassium hydroxide also fall within the scope of the present invention when they can be used. For other examples of pharmaceutically acceptable salts, reference can be made to "Salt selection for basic drugs", *Int. J. Pharm.* (1986), 33, 201-217.

A subject of the present application is also the use of the compounds according to the present invention, for the preparation of a medicament for the treatment of weight disorders such as obesity, cachexia and more particularly cachexia of cancerous pathologies, AIDS cachexia, cachexia in older persons, cardiac cachexia, renal cachexia, rheumatoid arthritis cachexia, and anorexia, the treatment of pain and more particularly neuropathic pain, mental disorders such as anxiety and depression, sexual activity disorders such as erectile disorders.

The pharmaceutical composition can be in the form of a solid, for example, powders, granules, tablets, gelatin capsules or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or the glycols, as well as their mixtures, in varying proportions, in water, added to pharmaceutically acceptable oils or fats. The sterile liquid compositions can be used for intramuscular, intraperitoneal or subcutaneous injections and the sterile compositions can also be administered intravenously.

All the technical and scientific terms used in the present text have the meaning known to a person skilled in the art.

Moreover, all the patents (or patent applications) as well as the other bibliographical references are incorporated by way of reference.

EXPERIMENTAL PART

The compounds according to the invention obtained according to the procedures of examples A, B, C and C' described previously, are shown in the table below.

The compounds are characterized by their retention time (rt) and their molecular peak determined by mass spectrometry (MH+).

For the mass spectrometry, a simple quadrupole mass spectrometer (Micromass, Platform model) equipped with an electrospray source is used with a resolution of 0.8 Da at 50% valley. A calibration is carried out monthly between the masses 80 and 1000 Da using a calibrating mixture of sodium iodide and rubidium iodide in solution in an isopropanol/water mixture (1/1 Vol.).

For the liquid chromatography, a Waters system including an in-line degasser, a Waters 600 quaternary pump, a Gilson 233 plate sampling injector and a Waters PAD 996 UV detector, is used.

The elution conditions used are the following:

| Eluent: A water + 0.04% trifluoroacetic acid; B acetonitrile | | |
| --- | --- | --- |
| T (min) | A % | B % |
| 1 | 95 | 5 |
| 8.5 | 5 | 95 |
| 10.5 | 5 | 95 |
| 10.6 | 95 | 5 |
| 14.9 | 95 | 5 |
| 15.0 | 95 | 5 |

Flow rate: 1 ml/min; Injection: 10 µl; Column: Uptisphere ODS 3 µm 75*4.6 mm i.d.

These examples are presented to illustrate the above procedures and should in no case be considered as a limit to the scope of the invention.

| Examples | Molecular structures | [M + H] + | rt (min) |
| --- | --- | --- | --- |
| 1 | 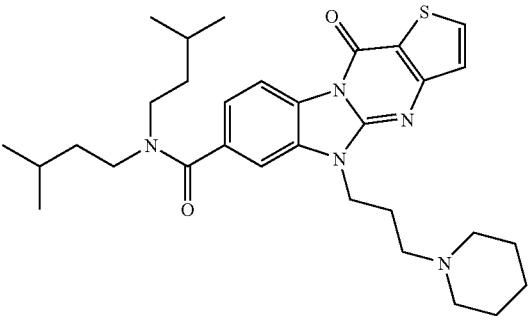 | 550.3 | 8.9 |
| 2 | 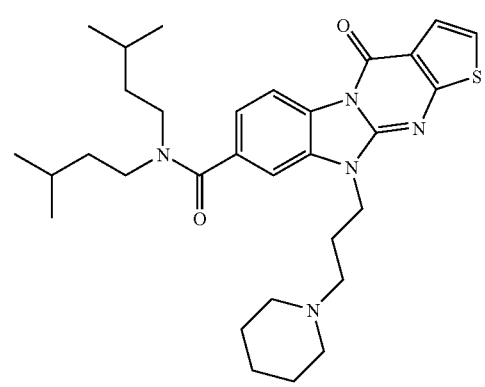 | 550.4 | 9.6 |

-continued
| Examples | Molecular structures | [M + H] + | rt (min) |
|---|---|---|---|
| 3 | 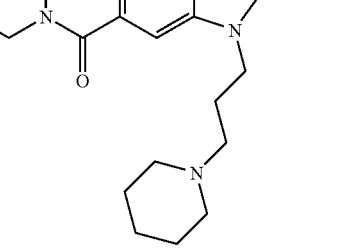 | 550.4 | 9.5 |
| 4 | 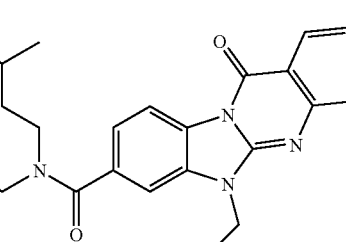 | 544.1 | 9.1 |
| 5 | 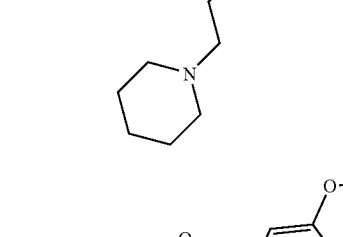 | 604.4 | 9.6 |
| 6 | 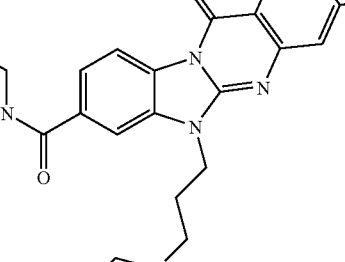 | 564.4 | 9.9 |

-continued
| Examples | Molecular structures | [M + H]+ | rt (min) |
|---|---|---|---|
| 7 | 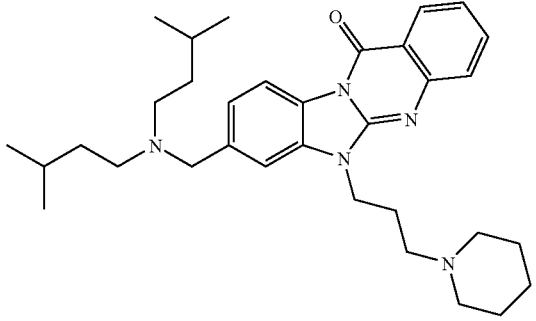 | 530.5 | 8.1 |
| 8 | 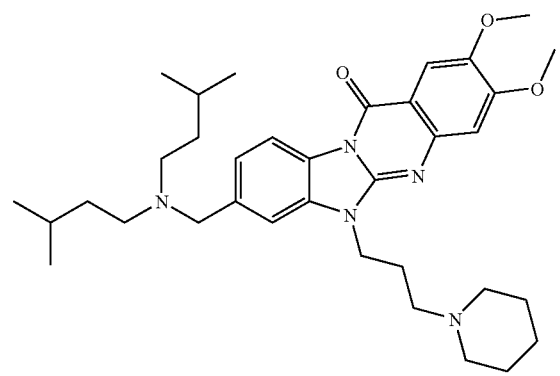 | 590.4 | 8.1 |
| 9 | 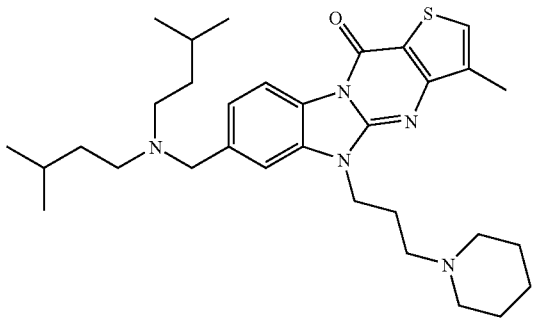 | 550.4 | 8.2 |
| 10 | 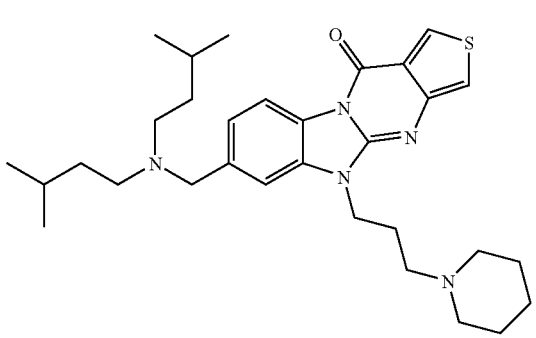 | 536.4 | 8.0 |

-continued

| Examples | Molecular structures | [M + H]+ | rt (min) |
|---|---|---|---|
| 11 | 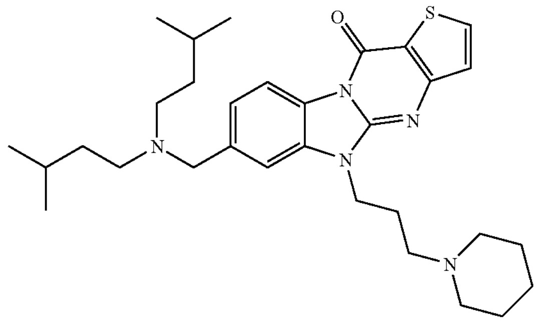 | 536.4 | 8.0 |
| 12 | 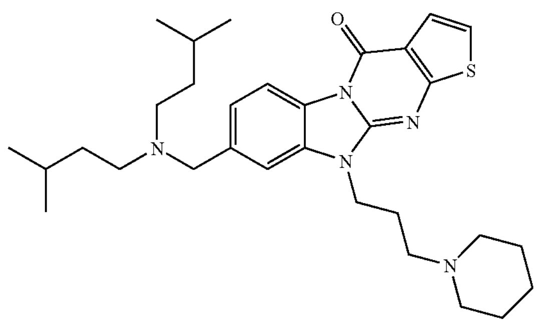 | 536.4 | 8.0 |
| 13 | 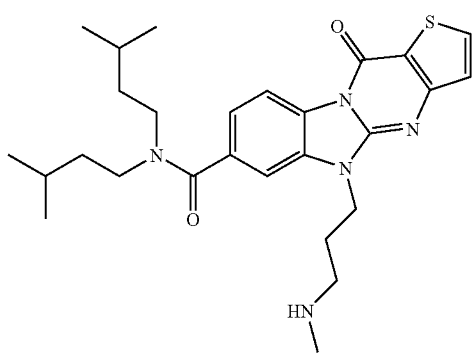 | 496.5 | 9.2 |
| 14 | 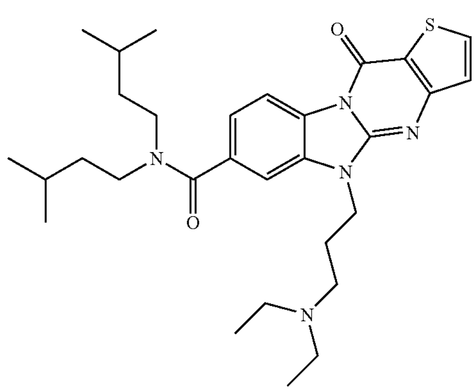 | 538.5 | 9.5 |

-continued

| Examples | Molecular structures | [M + H]+ | rt (min) |
|---|---|---|---|
| 15 | 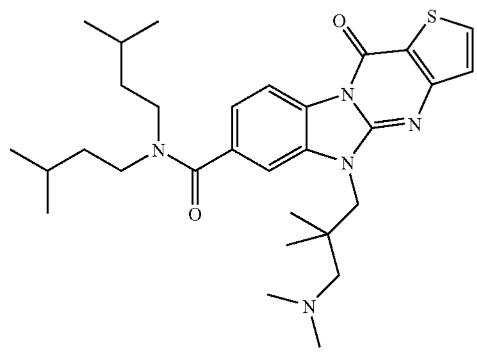 | 538.5 | 9.5 |
| 16 | 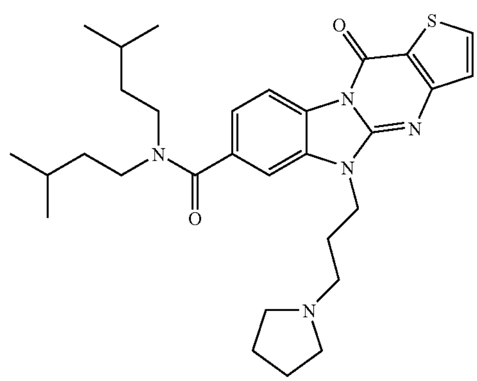 | 536.3 | 9.2 |
| 17 | 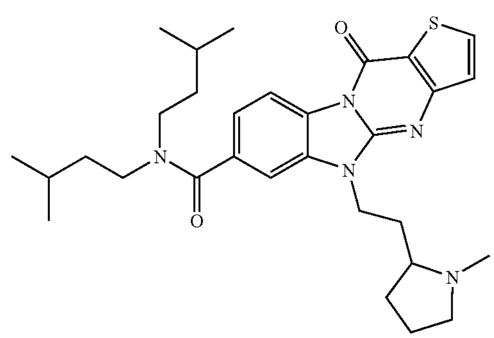 | 536.5 | 9.4 |
| 18 | 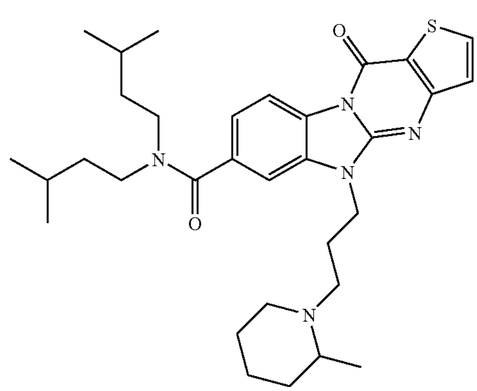 | 564.5 | 9.6 |

-continued

| Examples | Molecular structures | [M + H]+ | rt (min) |
|---|---|---|---|
| 19 | 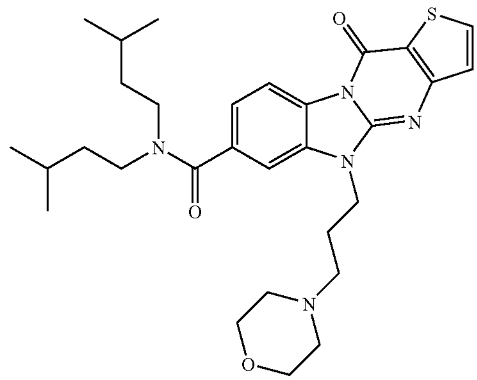 | 552.5 | 9.3 |
| 20 | 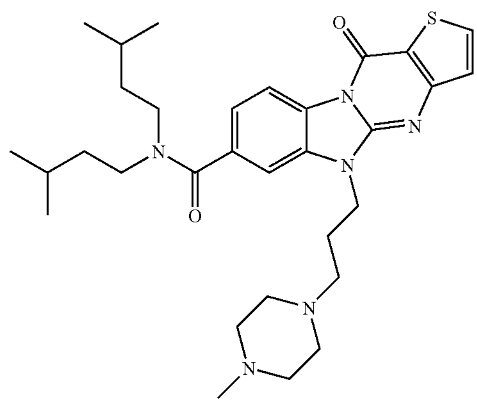 | 565.5 | 9.0 |
| 21 | 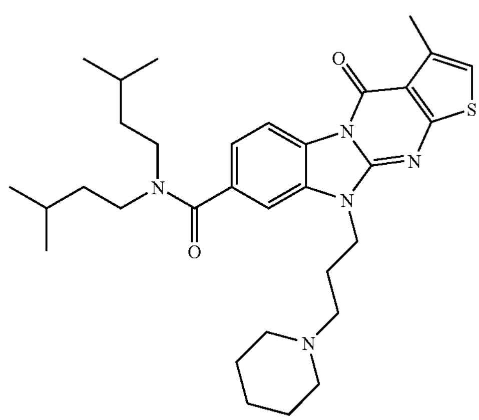 | 564.2 | 10.1 |
| 22 | 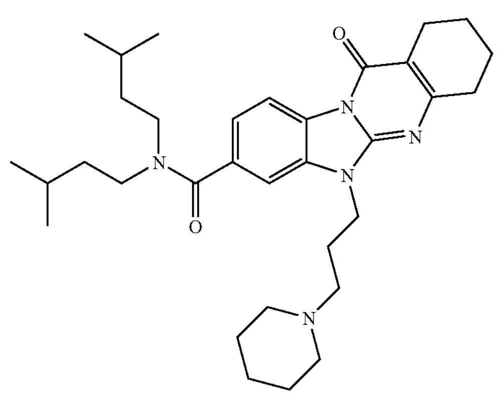 | 548.4 | 9.6 |

-continued
| Examples | Molecular structures | [M + H] + | rt (min) |
|---|---|---|---|
| 23 | 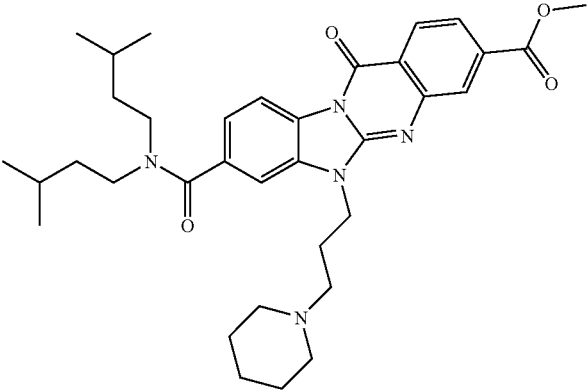 | 602.3 | 10.0 |
| 24 | 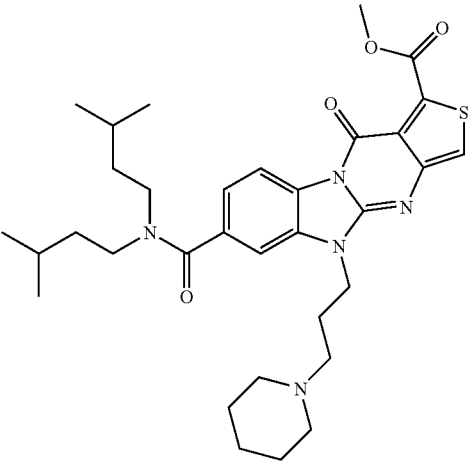 | 608.4 | 9.5 |
| 25 | 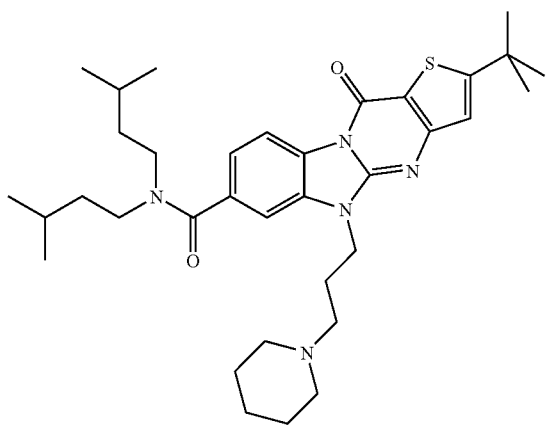 | 606.4 | 10.4 |

-continued

| Examples | Molecular structures | [M + H] + | rt (min) |
|---|---|---|---|
| 26 | 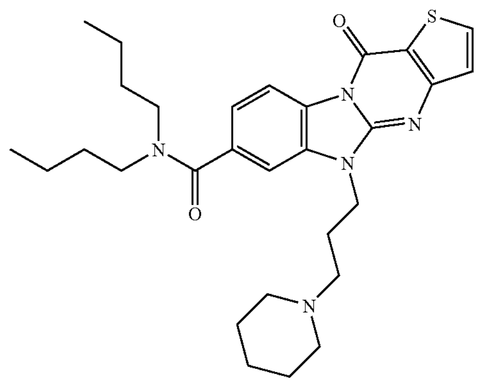 | 522.3 | 9.1 |
| 27 | 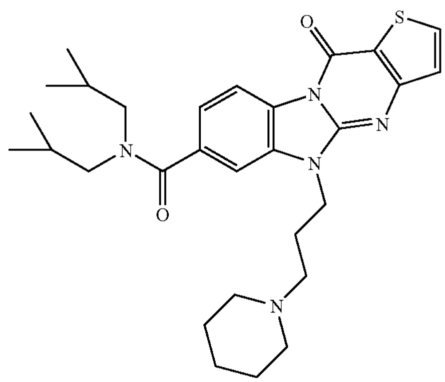 | 522.3 | 9.0 |
| 28 | 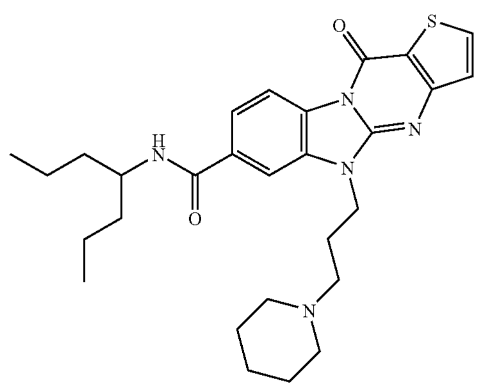 | 508.3 | 8.9 |
| 29 | 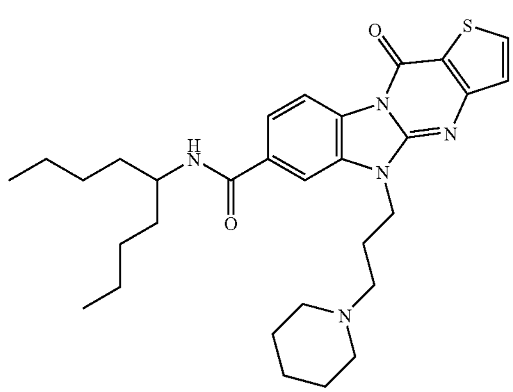 | 536.3 | 9.4 |

-continued

| Examples | Molecular structures | [M + H]+ | rt (min) |
| --- | --- | --- | --- |
| 30 | 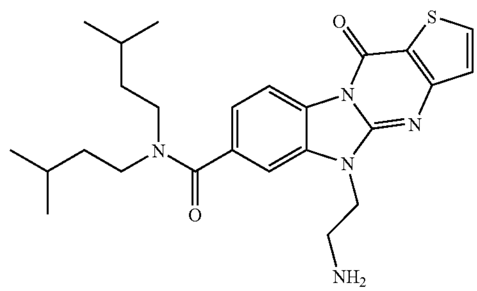 | 468.4 | 9.1 |
| 31 | 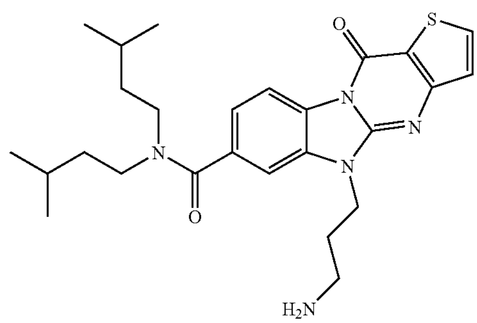 | 482.4 | 9.1 |
| 32 | 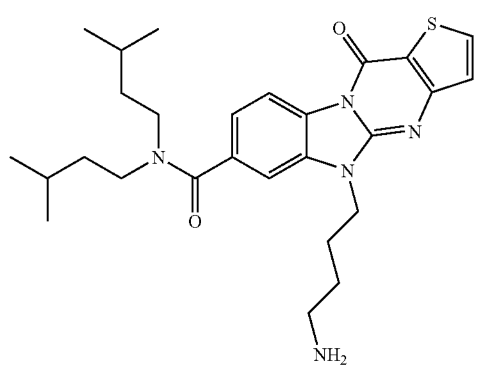 | 496.4 | 9.1 |
| 33 | 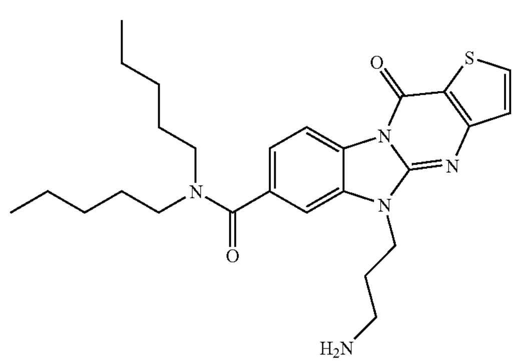 | 482.4 | 9.3 |

-continued

| Examples | Molecular structures | [M + H]+ | rt (min) |
| --- | --- | --- | --- |
| 34 | 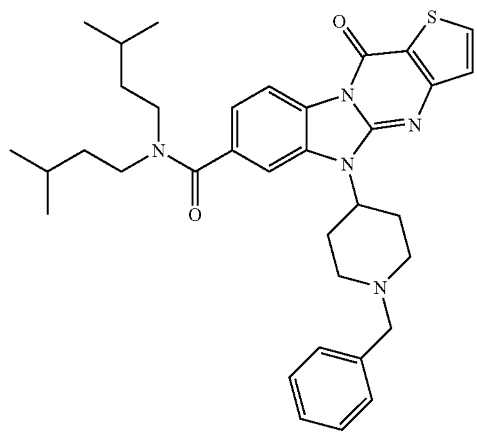 | 598.3 | 10.0 |
| 35 | 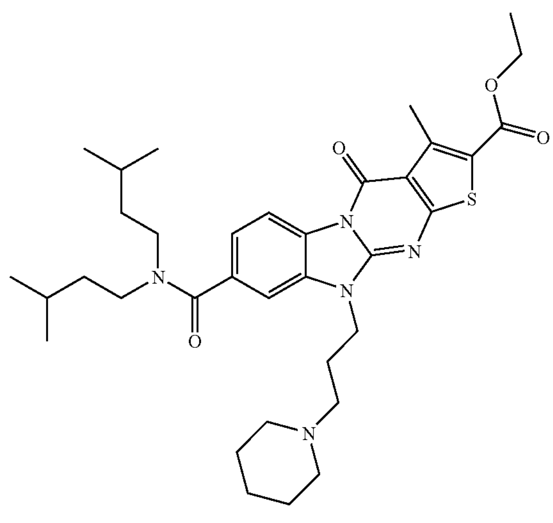 | 636.5 | 11.1 |
| 36 | 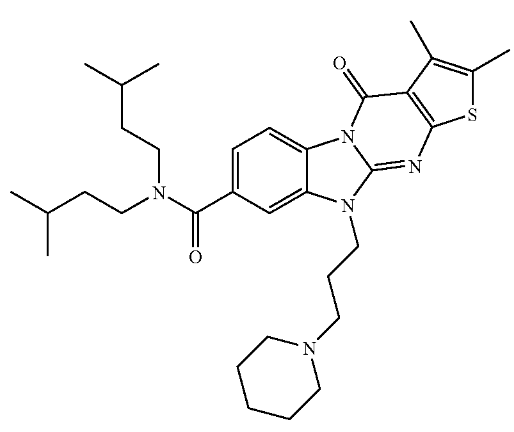 | 578.4 | 10.7 |

-continued

| Examples | Molecular structures | [M + H]+ | rt (min) |
| --- | --- | --- | --- |
| 37 | 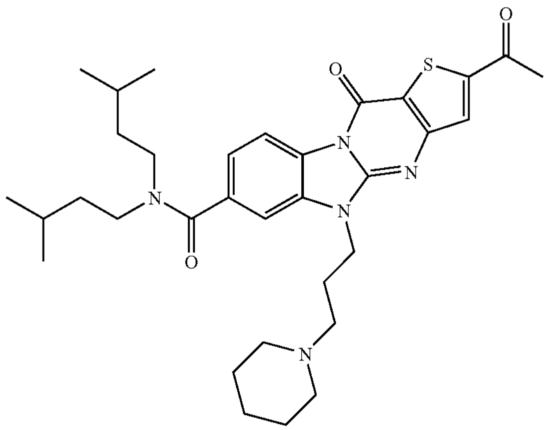 | 592.4 | 9.9 |
| 38 | 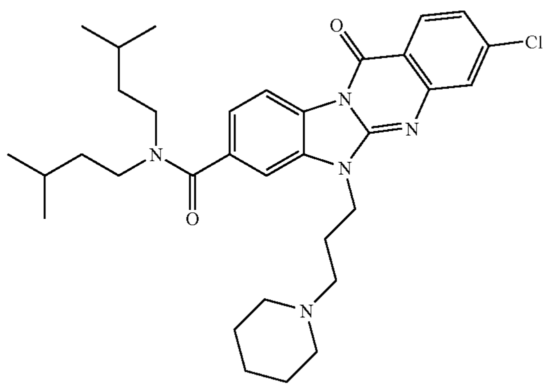 | 578.2 | 10.1 |
| 39 | 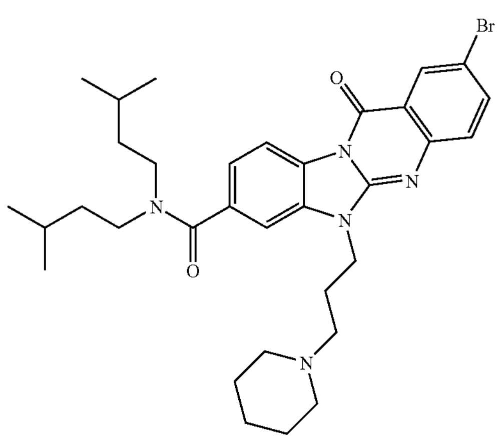 | 622.2 | 10.3 |

-continued
| Examples | Molecular structures | [M + H]+ | rt (min) |
|---|---|---|---|
| 40 | 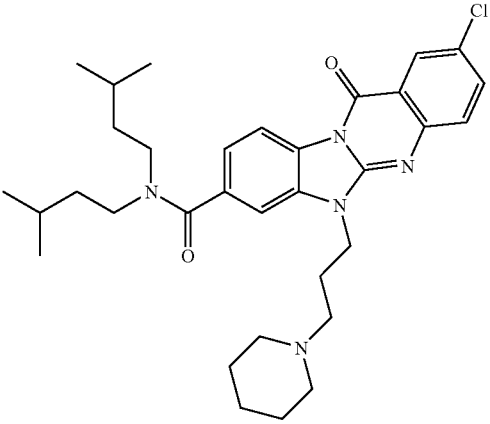 | 578.2 | 10.2 |
| 41 | 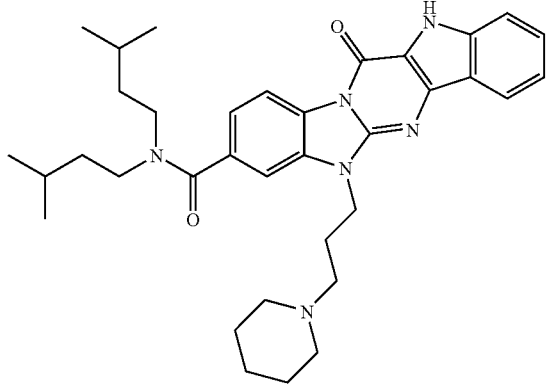 | 583.4 | 9.3 |
| 42 | 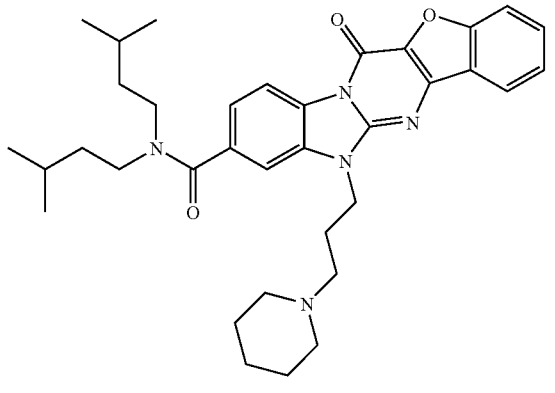 | 584.4 | 9.6 |
| 43 | 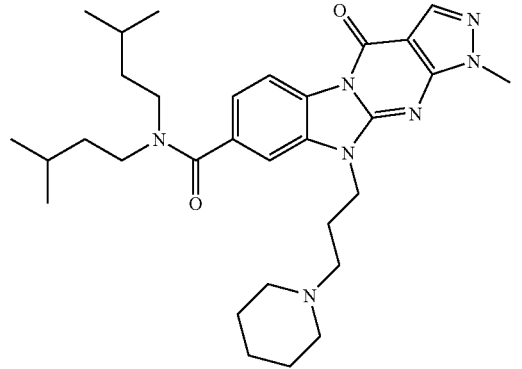 | 548.3 | 9.0 |

-continued
| Examples | Molecular structures | [M + H] + | rt (min) |
|---|---|---|---|
| 44 | 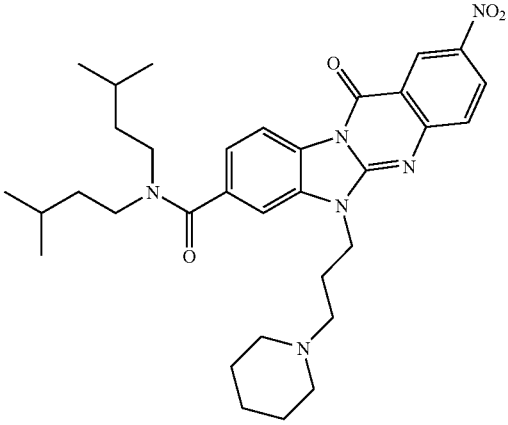 | 589.4 | 9.8 |
| 45 | 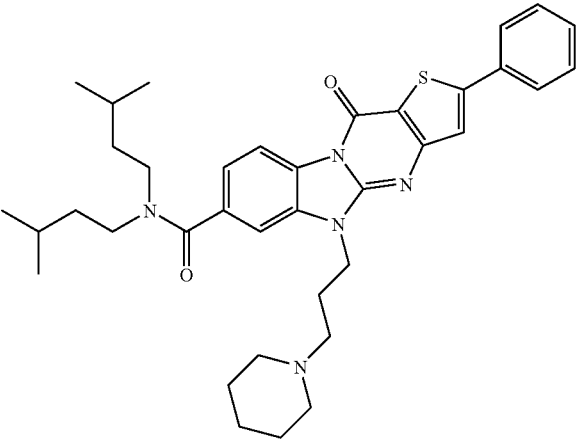 | 626.4 | 10.3 |
| 46 | 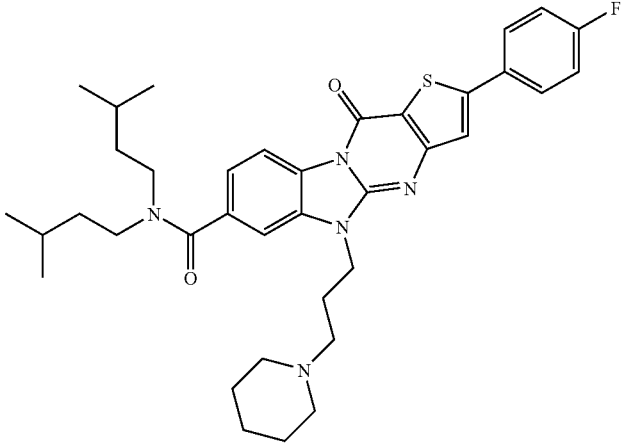 | 644.4 | 10.4 |

-continued
| Examples | Molecular structures | [M + H] + | rt (min) |
| --- | --- | --- | --- |
| 47 | 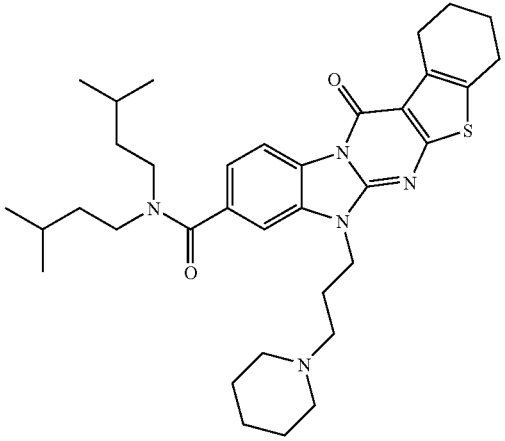 | 604.3 | 10.4 |
| 48 | 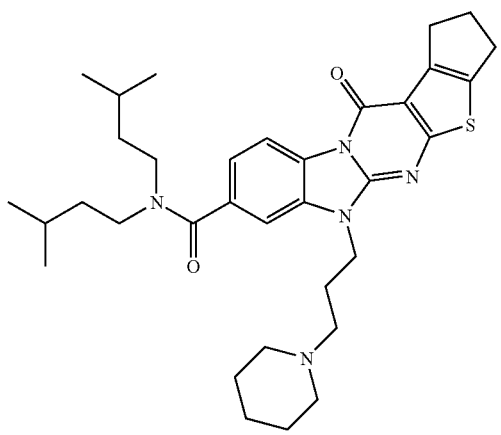 | 590.3 | 10.0 |
| 49 | 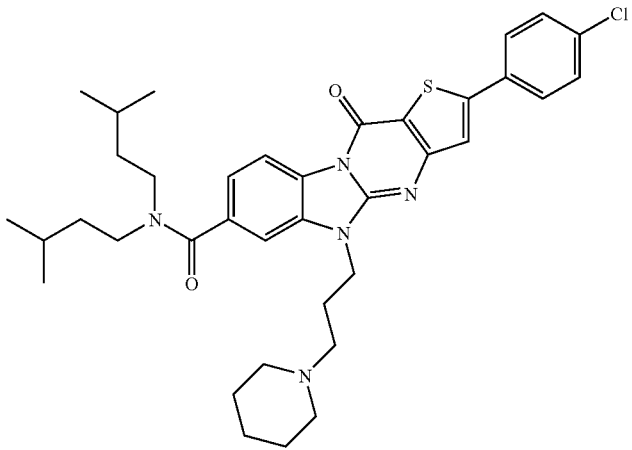 | 660.4 | 10.7 |

-continued

| Examples | Molecular structures | [M + H] + | rt (min) |
| --- | --- | --- | --- |
| 50 | 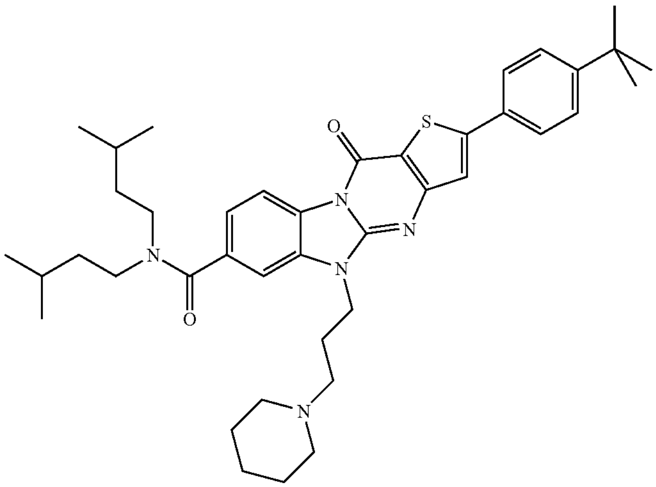 | 682.5 | 11.2 |
| 51 | 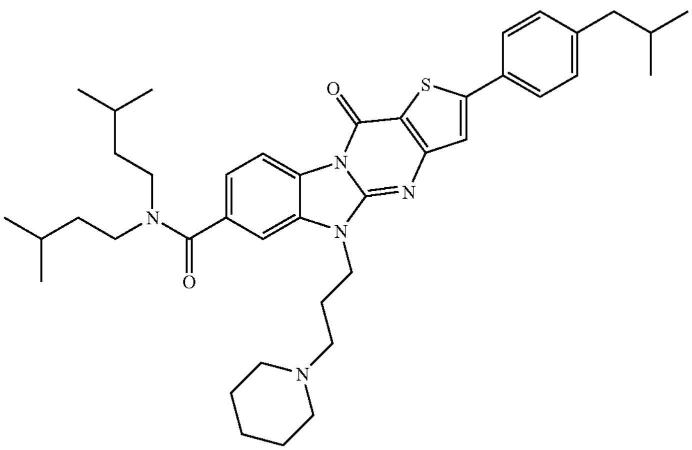 | 682.5 | 11.3 |
| 52 | 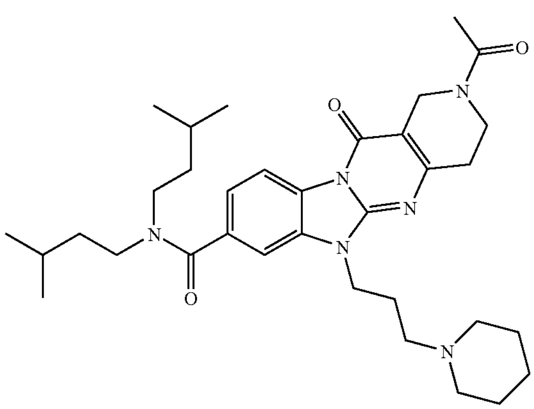 | 591.4 | 8.5 |

-continued
| Examples | Molecular structures | [M + H] + | rt (min) |
|---|---|---|---|
| 53 | 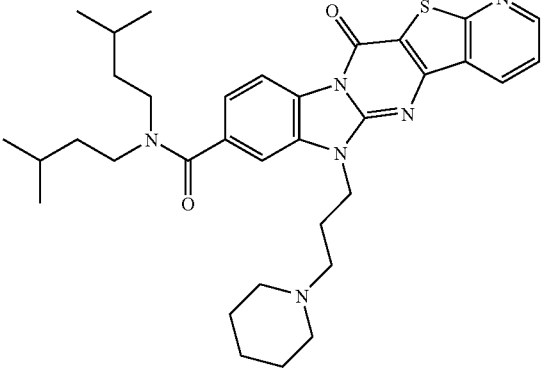 | 601.3 | 9.5 |
| 54 | 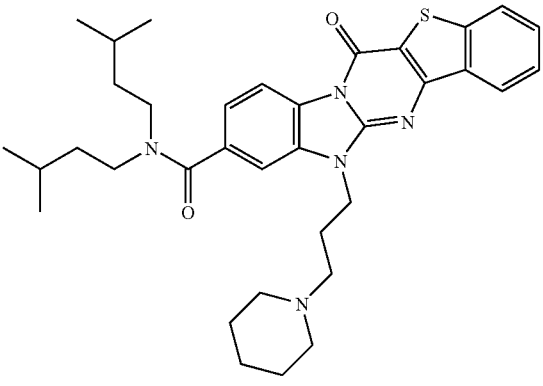 | 600.4 | 10.1 |
| 55 | 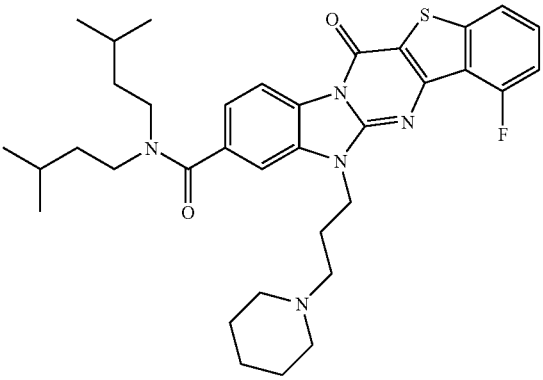 | 618.4 | 10.1 |
| 56 | 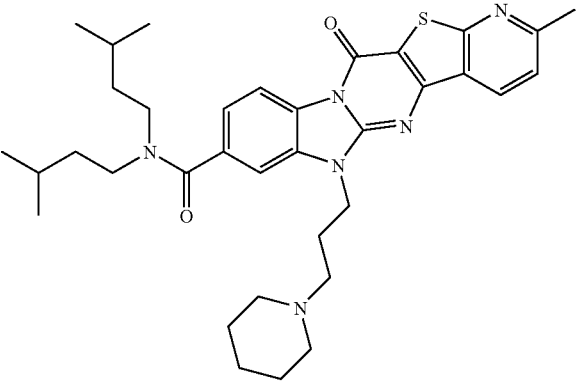 | 615.4 | 9.6 |

-continued
| Examples | Molecular structures | [M + H] + | rt (min) |
|---|---|---|---|
| 57 | 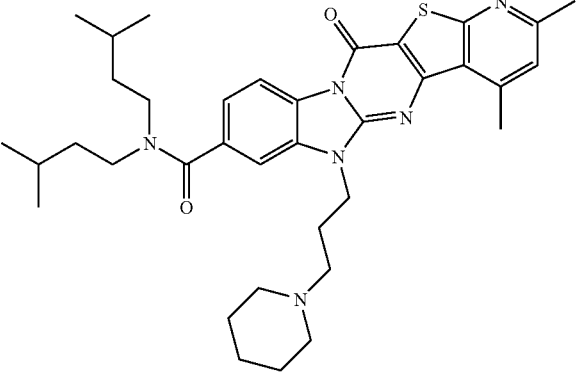 | 629.4 | 9.9 |
| 58 | 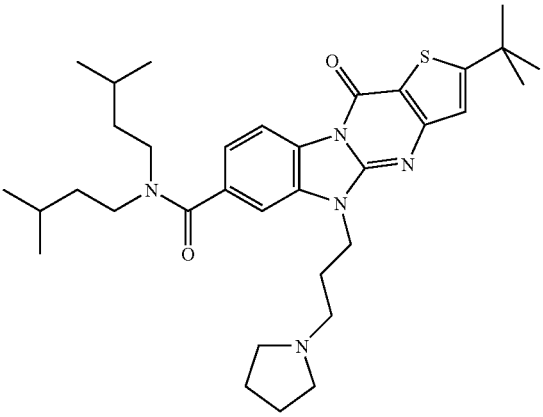 | 592.4 | 10.1 |
| 59 | 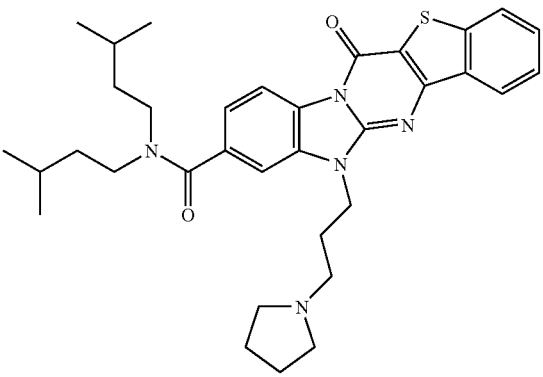 | 586.3 | 10.0 |

-continued
| Examples | Molecular structures | [M + H]+ | rt (min) |
|---|---|---|---|
| 60 | 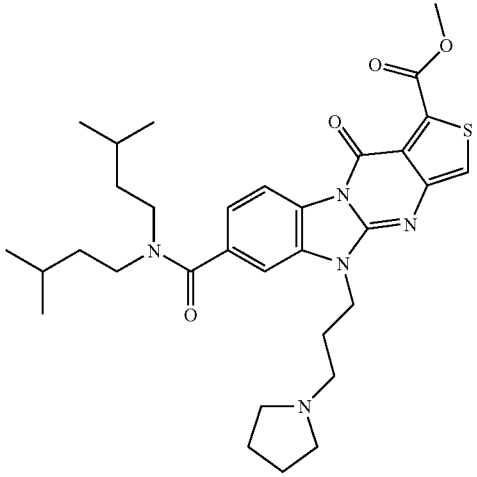 | 594.3 | 9.3 |
| 61 | 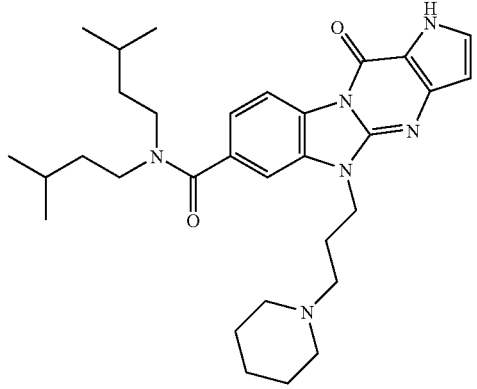 | 533.3 | 9.0 |
| 62 | 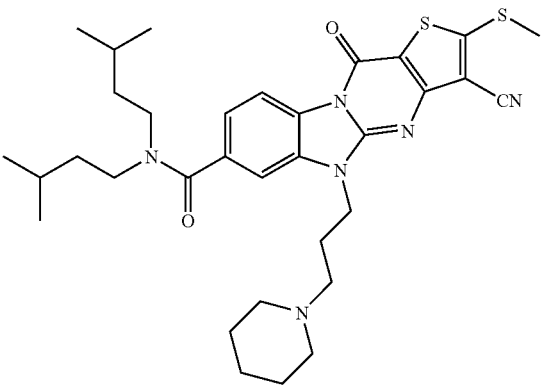 | 621.1 | 9.9 |

-continued

| Examples | Molecular structures | [M + H]+ | rt (min) |
| --- | --- | --- | --- |
| 63 | 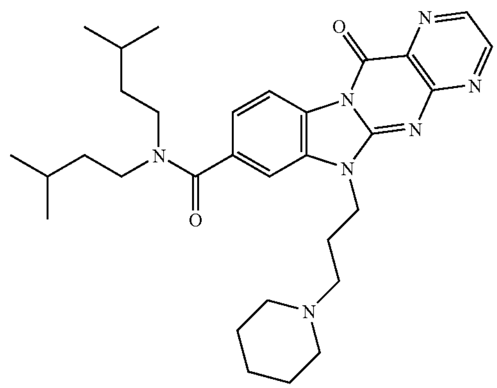 | 546.3 | 8.8 |
| 64 | 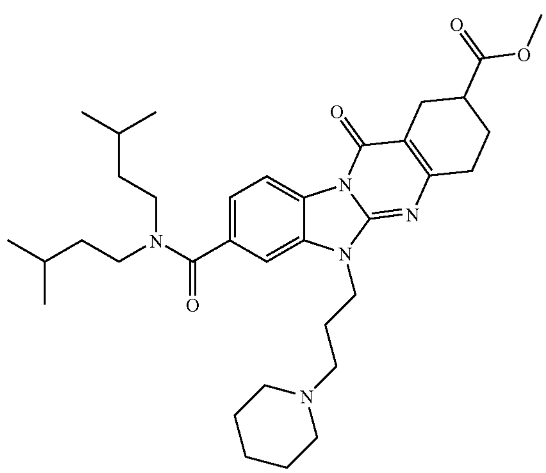 | 606.4 | 9.4 |
| 65 | 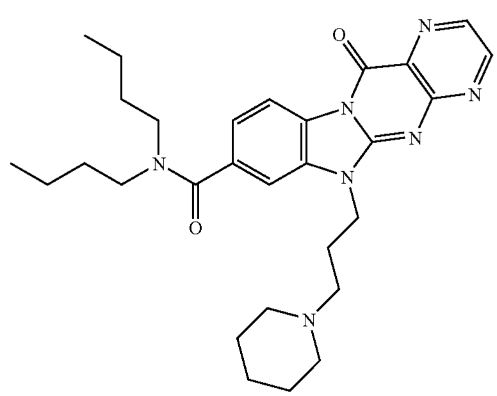 | 518.3 | 8.4 |

-continued

| Examples | Molecular structures | [M + H]+ | rt (min) |
|---|---|---|---|
| 66 | 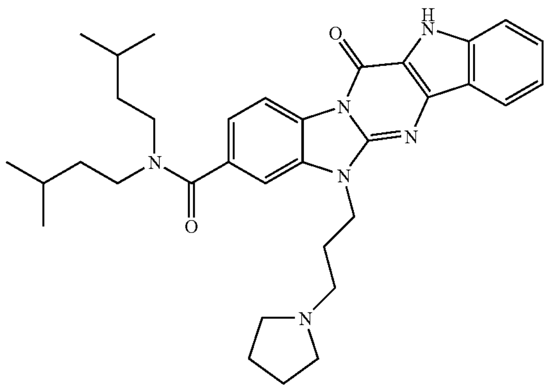 | 569.4 | 9.4 |
| 67 | 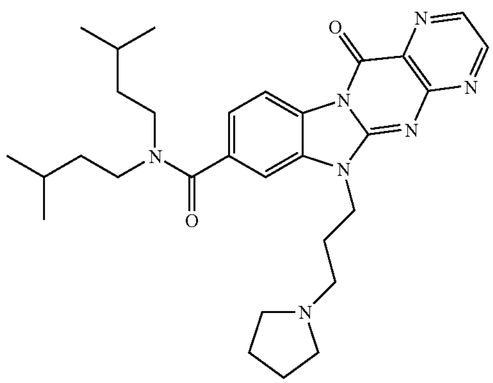 | 532.4 | 8.9 |
| 68 | 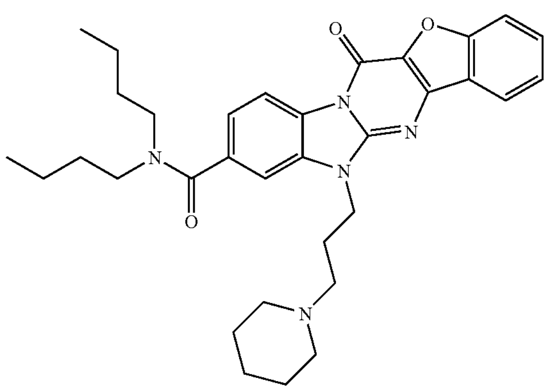 | 556.4 | 9.6 |
| 69 | 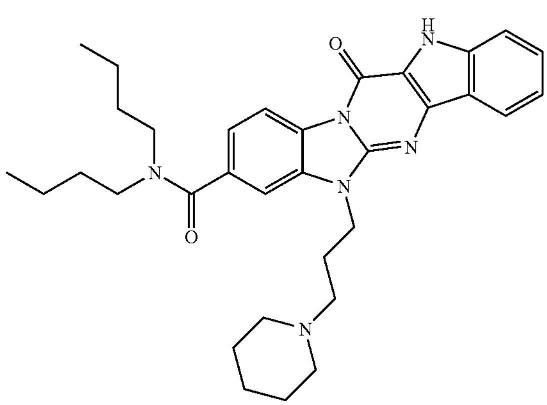 | 554.4 | 9.1 |

-continued

| Examples | Molecular structures | [M + H] + | rt (min) |
|---|---|---|---|
| 70 | 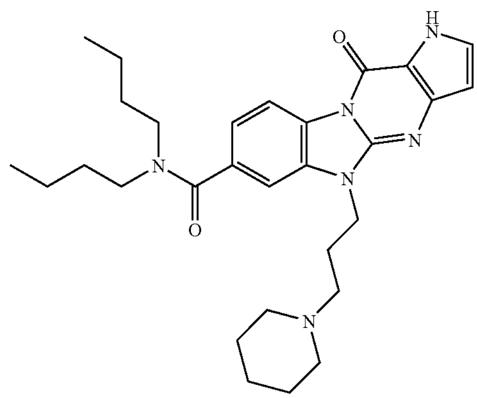 | 505.4 | 8.5 |
| 71 | 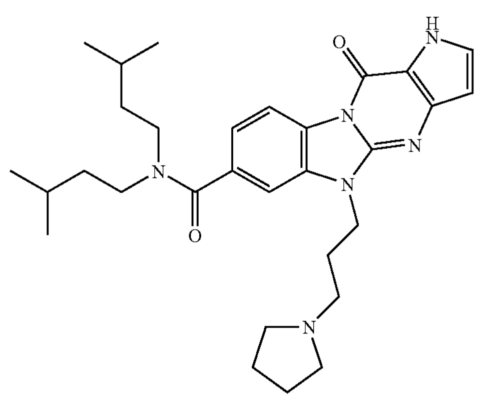 | 519.4 | 8.9 |
| 72 | 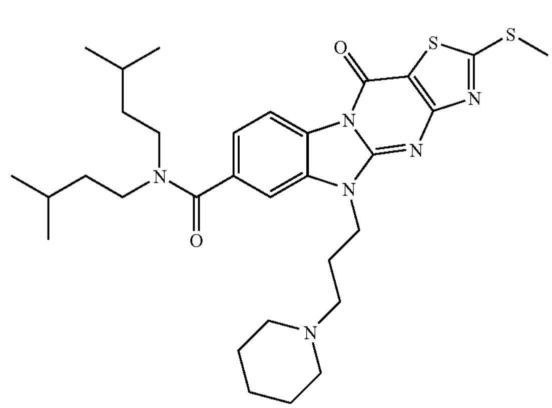 | 597.4 | 9.9 |

-continued
| Examples | Molecular structures | [M + H]+ | rt (min) |
|---|---|---|---|
| 73 | 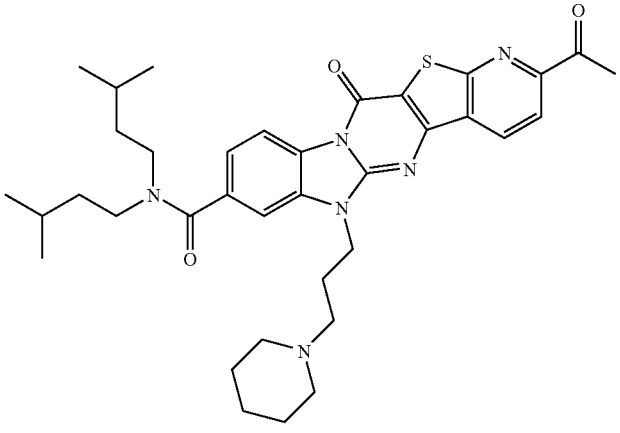 | 643.4 | 10.3 |
| 74 | 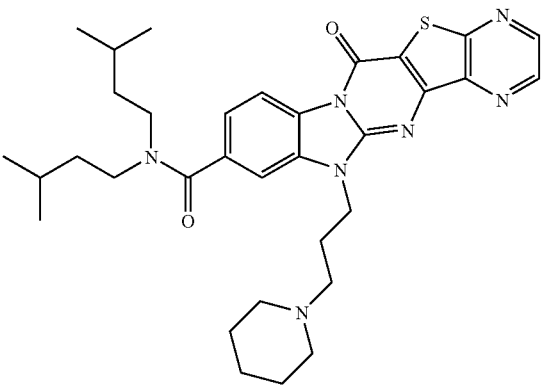 | 602.4 | 9.6 |
| 75 | 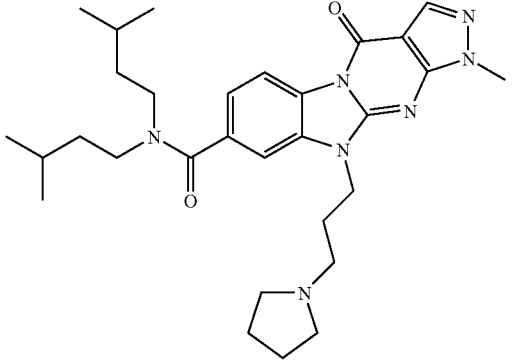 | 534.4 | 9.1 |

-continued

| Examples | Molecular structures | [M + H]+ | rt (min) |
|---|---|---|---|
| 76 | 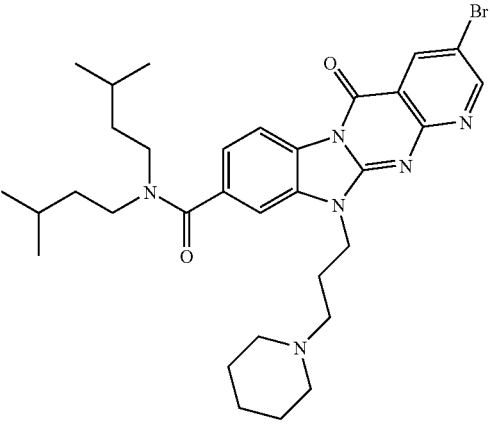 | 623.3 | 9.7 |
| 77 | 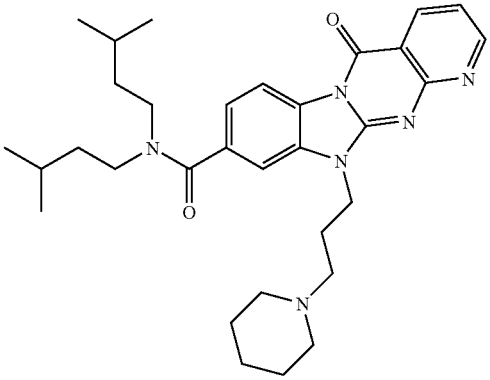 | 545.4 | 9.0 |
| 78 | 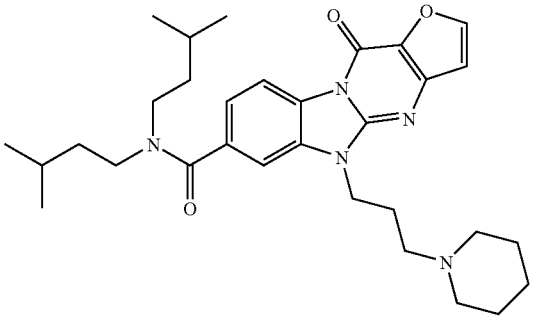 | 534.3 | 9.1 |

Pharmacological Study

The affinity of the compounds of the present invention for the different sub-types of melanocortin receptors was measured according to procedures analogous to those described below for the MC4 receptors.

Study of the Affinity of the Compounds for the MC4 Receptors of Melanocortins:

The affinity of the compounds of the invention for the MC4 receptors is determined by measuring the inhibition of the binding of [$^{125}$I]-[Nle$^4$, D-Phe$^7$]-α-MSH to membrane preparations of transfected CHO-K1 cells.

The CHO-K1 cells expressing in a stable fashion the human MC4 receptors are cultured in an RPMI 1640 medium containing 10% of fetal calf serum, 2 mM of glutamine, 100 U/ml of penicillin, 0.1 mg/ml of streptomycin and 0.5 mg/ml of G418. The cells are collected with 0.5 mM of EDTA and centrifuged at 500 g for 5 minutes at 4° C. The pellet is resuspended in a phosphate buffered saline (PBS) medium and centrifuged at 500 g for 5 minutes at 4° C. The pellet is resuspended in a Tris 50 mM buffer medium at pH 7.4 and centrifuged at 500 g for 5 minutes at 4° C. The cells are lysed by sonication and centrifuged at 39,000 g for 10 minutes at 4° C. The pellet is resuspended in the Tris 50 mM buffer medium at pH 7.4 and centrifuged at 50,000 g for 110 min at 4° C. The membranes obtained in this last pellet are stored at −80° C.

The measurement of the competitive inhibition of the binding of [$^{125}$I]-[Nle$^4$, D-Phe$^7$]-α-MSH to the MC4 receptors is carried out in duplicate using polypropylene 96-well plates. The cell membranes (50 μg of proteins/well) are incubated with [$^{125}$I]-Nle$^4$, D-Phe$^7$)-α-MSH (0.5 nM) for 90 minutes at 37° C. in a Tris-HCl 50 mM buffer medium, pH 7.4, comprising 0.2% of bovine serum albumin (BSA), 5 mM of $MgCl_2$, and 0.1 mg/ml of bacitracin.

The bonded $[^{125}I]$-$[Nle^4, D$-$Phe^7]$-$\alpha$-MSH is separated from the free $[^{125}I]$-$[Nle^4, D$-$Phe^7]$-$\alpha$-MSH by filtration through GF/C glass fibre filters (Unifilter, Packard) pre-impregnated with 0.1% of polyethylenimine (P.E.I.), using a Filtermate 196 (Packard). The filters are washed with Tris-HCl 50 mM buffer, pH 7.4 at 0-4° C. and the radioactivity present is determined using a counter (Packard Top Count).

The specific binding is obtained by subtracting the non-specific binding (determined in the presence of 0.1 µM of $Nle^4$, $D$-$Phe^7$-$\alpha$-MSH) from the total binding. The data are analyzed by computer-aided non-linear regression (MDL) and the values of the inhibition constants (Ki) are determined.

The agonist or antagonist activity of the MC4 receptors of the compounds of the present invention was determined by measuring the production of cyclic AMP by the CHO-K1 cells transfected by the MC4 receptor.

Measurement of the Production of Intracellular Cyclic AMP Via the MC4 Receptors:

The CHO-K1 cells expressing the MC4 receptors of the melanocortins are cultured in 384-well plates in an RPMI 1640 medium with 10% of fetal calf serum and 0.5 mg/ml of G418. The cells are washed twice with 50 µl of RPMI medium comprising 0.2% BSA and 0.5 mM of 3-isobutyl-1-methylxanthine (IBMX).

In order to measure the agonist effect of a compound, the cells are incubated for 5 minutes at 37° C. in the presence of 0.5 mM of IBMX, then stimulation of the production of cyclic AMP is obtained by adding the compound at concentrations comprised between 1 pM and 10 µM in duplicate for 20 minutes at 37° C. The antagonist effect of a compound is measured by inhibiting stimulation of the production of cyclic AMP induced by $Nle^4$, $D$-$Phe^7$-$\alpha$-MSH at concentrations comprised between 1 pM and 10 µm, in the presence of the compound to be tested, at concentrations comprised between 1 nM and 10 µM in duplicate for 20 minutes at 37° C.

The reaction medium is eliminated and 80 µl of lysis buffer is added. The intracellular cyclic AMP level is measured by a competition test with fluorescent cyclic AMP (CatchPoint, Molecular Devices).

The tests carried out according to the protocols described above have made it possible to show that the products according to the present invention have a good affinity for the MC4 receptors, the inhibition constant $K_i$ on these receptors being less than micromolar for the majority of the compounds exemplified.

The invention claimed is:

1. A compound of formula (I)

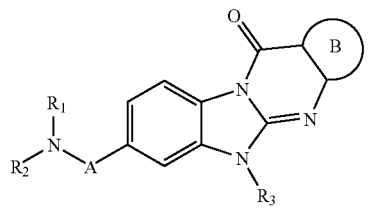

(I)

in racemic or enantiomeric form or any combinations of thereof, wherein:

A is —$CH_2$— or —C(O)—;

$R_1$ is a hydrogen atom; a ($C_1$-$C_8$) alkyl radical optionally substituted by hydroxy or one or more identical or different halo radicals; ($C_2$-$C_6$) alkenyl; or a radical of formula —$(CH_2)_n$—$X_1$;

$R_2$ is a ($C_1$-$C_8$) alkyl radical optionally substituted by hydroxy or one or more identical or different halo radicals; ($C_2$-$C_6$) alkenyl; or a radical of formula —$(CH_2)_n$—$X_1$;

each $X_1$ is, independently, a ($C_1$-$C_6$) alkoxy, ($C_3$-$C_7$) cycloalkyl, adamantyl, heterocycloalkyl, aryl or heteroaryl radical, the ($C_3$-$C_7$) cycloalkyl, heterocycloalkyl, aryl and heteroaryl radicals being optionally substituted by one or more identical or different substituents including —$(CH_2)_n$—$V_1$—$Y_1$, halo, nitro, cyano or aryl;

$V_1$ is —O—, —S— or a covalent bond;

$Y_1$ represents is a ($C_1$-$C_6$) alkyl radical optionally substituted by one or more identical or different halo radicals;

n is an integer from 0 to 6 and n' an integer from 0 to 2 with the proviso that when n is equal to 0, $X_1$ is not an alkoxy radical;

or $R_1$ and $R_2$ form, together with the nitrogen atom to which they are attached, a heterobicycloalkyl or a heterocycloalkyl optionally substituted by one or more identical or different substituents including hydroxy, ($C_1$-$C_6$) alkyl optionally substituted by hydroxy, ($C_1$-$C_6$) alkoxy-carbonyl, heterocycloalkyl or —C(O)—$NV_1'Y_1'$ wherein $V_1'$ and $Y_1'$ are, independently, a hydrogen atom or a ($C_1$-$C_6$) alkyl; or a radical of formula:

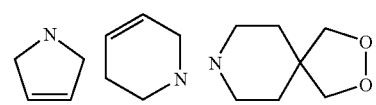

$R_3$ is a radical of formula —$(CH_2)_s$—$R'_3$;

$R'_3$ is a guanidino radical; a heterocycloalkyl comprising at least one nitrogen atom and optionally substituted by ($C_1$-$C_6$) alkyl or aralkyl; a heteroaryl comprising at least one nitrogen atom and optionally substituted by ($C_1$-$C_6$) alkyl; or a radical of formula —$NW_3W'_3$ $W_3$ is a hydrogen atom or ($C_1$-$C_8$) alkyl;

$W'_3$ is a radical of formula —$(CH_2)_s$—$Z_3$;

$Z_3$ is a hydrogen atom, ($C_1$-$C_8$) alkyl optionally substituted by one or more identical or different substituents including a ($C_1$-$C_6$) alkoxy, ($C_1$-$C_6$) alkylthio; hydroxy; ($C_2$-$C_6$) alkenyl; ($C_3$-$C_7$) cycloalkyl optionally substituted by one or more identical or different ($C_1$-$C_6$) alkyl substituents; cyclohexene; heteroaryl or aryl;

the aryl and heteroaryl radicals being optionally substituted by one or more identical or different radicals including: a radical of formula —$(CH_2)_{s''}$—$V_3$—$Y_3$, hydroxy, halo, nitro or cyano;

$V_3$ is —O—, —S—, —NH—C(O)—, —$NV'_3$ or a covalent bond;

$Y_3$ is a hydrogen atom or a ($C_1$-$C_6$) alkyl radical optionally substituted by one or more identical or different halo radicals;

$V'_3$ is a hydrogen atom or a ($C_1$-$C_6$) alkyl;

s'' is an integer from 0 to 4;

or Z₃ is a radical of formula

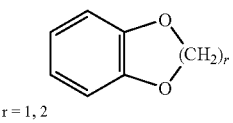

r = 1, 2 s and s' are, independently, an integer from 0 to 6;

B is a condensed, unsaturated, aromatic or non-aromatic mono- or bi-cyclic radical, optionally comprising one or more identical or different heteroatoms including O, S and N, and optionally substituted by one or more radicals, identical or different, including halo, nitro, cyano, oxy, —X$_B$—Y$_B$, or aryl optionally substituted by one or more substituents including halo and (C$_1$-C$_6$) alkyl optionally substituted by one or more identical or different halo radicals;

X$_B$ is a covalent bond, —O—, —S—, —C(O)—, —NR$_N$C(O)—, —C(O)—NR$_N$, —C(O)—O—, —SO$_2$— or —SO$_2$NH—;

Y$_B$ is a hydrogen atom or a (C$_1$-C$_6$) alkyl radical optionally substituted by one or more identical or different halo radicals;

R$_N$ is a hydrogen atom or a (C$_1$-C$_6$)alkyl radical;

or a pharmaceutically acceptable salt thereof.

2. The compound according to claim 1 wherein A is —C(O)—; or a pharmaceutically acceptable salt thereof.

3. The compound according to claim 1, wherein R$_1$ and R$_2$ are, independently, a (C$_1$-C$_8$) alkyl radical; or a pharmaceutically acceptable salt thereof.

4. The compound according to claim 1, wherein R$_1$ and R$_2$ are, independently, a (C$_1$-C$_6$) alkyl radical; or a pharmaceutically acceptable salt thereof.

5. The compound according to claim 1, wherein R$_1$ and R$_2$ are, independently, a butyl, pentyl or isopentyl radical; or a pharmaceutically acceptable salt thereof.

6. The compound according to claim 1, wherein R'$_3$ is a heterocycloalkyl comprising at least one nitrogen atom and optionally substituted by (C$_1$-C$_6$) alkyl or benzyl; or a radical of formula —NW$_3$W'$_3$ wherein W$_3$ is a hydrogen atom or a (C$_1$-C$_8$) alkyl radical, and W'$_3$ is a Z$_3$ radical and Z$_3$ is a hydrogen atom or a (C$_1$-C$_8$) alkyl radical; or a pharmaceutically acceptable salt thereof.

7. The compound according to claim 1, wherein B is a radical including phenyl, thienyl, pyrrolyl, pyrazolyl, pyridyl, pyrimidyl, pyrazinyl, benzothienyl, thieno-pyridinyl, thieno-pyrazinyl, indolyl, benzofuryl, cyclopentenyl, cyclohexenyl, 1,2,3,6-tetrahydropyridinyl, 1,2,3,4-tetrahydropyrimidinyl, 4,5,6,7-tetrahydro-thieno[2,3-c]pyridinyl, tetrahydrobenzothienyl or dihydrocyclopentathienyl.

8. The compound according to claim 7, wherein B is optionally substituted by one or more radicals, identical or different, including: halo, nitro, cyano, oxy, —X$_B$—Y$_B$, or phenyl optionally substituted by one or more substituents including halo or (C$_1$-C$_6$) alkyl optionally substituted by one or more identical or different halo radicals;

X$_B$ is a covalent bond, —O—, —S—, —C(O)—, —NR$_N$—C(O)— or —C(O)—O—;

Y$_B$ is a hydrogen atom or a (C$_1$-C$_6$) alkyl radical optionally substituted by one or more identical or different halo radicals;

R$_N$ is a hydrogen atom; or a pharmaceutically acceptable salt thereof.

9. The compound according to claim 1, wherein B is a radical including phenyl, furyl, thienyl, pyrrolyl, pyrazolyl, pyridyl, thiazolyl, pyrazinyl, benzothienyl, thieno-pyridinyl, thieno-pyrazinyl, indolyl, benzofuryl, cyclohexenyl, 1,2,3,6-tetrahydropyridinyl, tetrahydrobenzothienyl or dihydrocyclopentathienyl.

10. The compound according to claim 9, wherein B is optionally substituted by one or more radicals, identical or different, including halo, nitro, cyano, —X$_B$—Y$_B$, or phenyl optionally substituted by one or more substituents including halo or (C$_1$-C$_6$) alkyl;

X$_B$ is a covalent bond, —O—, —S—, —C(O)—, or —C(O)—O—;

Y$_B$ is a hydrogen atom or a (C$_1$-C$_6$) alkyl radical; or a pharmaceutically acceptable salt thereof.

11. The compound according to claim 1, wherein B is a radical including phenyl, furyl, thienyl, pyrrolyl, pyrazolyl, pyridyl, pyrazinyl, benzothienyl, thieno-pyridinyl, indolyl, benzofuryl, cyclohexenyl, 1,2,3,6-tetrahydropyridinyl, tetrahydrobenzothienyl or dihydrocyclopentathienyl.

12. The compound according to claim 11, wherein B is optionally substituted by one or more radicals, identical or different, including halo, nitro or —X$_B$—Y$_B$; X$_B$ is a covalent bond, —O—, —C(O)— or —C(O)—O—; Y$_B$ is a (C$_1$-C$_6$) alkyl radical; or a pharmaceutically acceptable salt thereof.

13. The compound according to claim 12, wherein B is optionally substituted by one or more radicals, identical or different, including halo, nitro or —X$_B$—Y$_B$; X$_B$ is a covalent bond or —O— and Y$_B$ is a (C$_1$-C$_6$) alkyl radical; or a pharmaceutically acceptable salt thereof.

14. The compound according to claim 1, wherein R'$_3$ is a heterocycloalkyl comprising at least one nitrogen atom and optionally substituted by (C$_1$-C$_6$) alkyl; or a pharmaceutically acceptable salt thereof.

15. The compound according to claim 14, wherein R'$_3$ is a piperidinyl or pyrrolidinyl radical; or a pharmaceutically acceptable salt thereof.

16. The compound according to claim 1, wherein R'$_3$ is a heterocycloalkyl with 5 to 6 members and comprising a single nitrogen atom and optionally an oxygen atom; or a radical of formula —NW$_3$W'$_3$ wherein W$_3$ is a hydrogen atom or a (C$_1$-C$_6$) alkyl radical, W'$_3$ is a Z$_3$ radical and Z$_3$ is a hydrogen atom or a (C$_1$-C$_6$) alkyl radical; or a pharmaceutically acceptable salt thereof.

17. The compound according to claim 16, wherein R'$_3$ is a piperidinyl or pyrrolidinyl radical and s is an integer from 2 to 4; or a pharmaceutically acceptable salt thereof.

18. The compound according to claim 1, wherein B is a radical including: phenyl, thienyl, pyrrolyl, pyrazolyl, pyridyl, benzothienyl, thieno-pyridinyl, thieno-pyrazinyl, indolyl, benzofuryl, cyclohexenyl, 4,5,6,7-tetrahydro-thieno[2,3-c]pyridinyl or dihydrocyclopentathienyl.

19. A method for the preparation of a compound of formula (I) according to claim 1, comprising treating a compound of general formula:

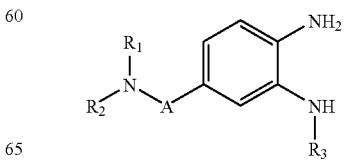

with an ortho-ester isothiocyanate of general formula:

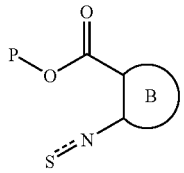

wherein P is a protective group;

in the presence of a coupling agent or yellow mercury (II) oxide in the presence of sulphur, a protic or aprotic solvent, and optionally in the presence of a base.

20. A pharmaceutical composition comprising a compound according to claim 1 as an active ingredient.

21. The method according to claim 19, wherein the protective group (P) is a methyl, ethyl, or tert-butyl group.

* * * * *